(12) United States Patent
Chen et al.

(10) Patent No.: US 11,191,473 B1
(45) Date of Patent: Dec. 7, 2021

(54) GENERATION OF VITAL SIGN MONITORING

(71) Applicants: Guangren Chen, Arcadia, CA (US);
Jia Li Chen, Palm Harbor, FL (US);
Rong Yang, Porter Ranch, CA (US)

(72) Inventors: Guangren Chen, Arcadia, CA (US);
Jia Li Chen, Palm Harbor, FL (US);
Rong Yang, Porter Ranch, CA (US)

( * ) Notice: Subject to any disclaimer, the term of this patent is extended or adjusted under 35 U.S.C. 154(b) by 282 days.

(21) Appl. No.: 16/595,395

(22) Filed: Oct. 7, 2019

Related U.S. Application Data

(63) Continuation-in-part of application No. 16/561,304, filed on Sep. 9, 2019, which is a continuation-in-part of application No. 16/157,178, filed on Oct. 11, 2018, now Pat. No. 10,729,351, which is a continuation-in-part of application No. 16/114,025, filed on Aug. 27, 2018, now Pat. No. 10,646,130, which is a continuation-in-part of application No. 15/998,487, filed on Aug. 16, 2018, now Pat. No. 10,631,750, which is a continuation-in-part of application No. 15/961,952, filed on Apr. 25, 2018, now Pat. No. 10,092,201, which is a continuation-in-part of application No. 15/904,543, filed on Feb. 26, 2018, now Pat. No. 10,085,663, which is a continuation-in-part of application No. 15/393,135, filed on Dec. 28, 2016, now Pat. No. 9,999,364, which is a continuation-in-part of application No. 14/749,697, filed on Jun. 25, 2015, now Pat. No. 9,538,930, which is a continuation-in-part of application No. 14/662,996, filed on Mar. 19, 2015, now Pat. No. 9,339,204, (Continued)

(51) Int. Cl.
| | | |
|---|---|---|
| A61B 5/364 | (2021.01) | |
| A61B 5/316 | (2021.01) | |
| A61B 5/366 | (2021.01) | |
| A61B 5/339 | (2021.01) | |

(52) U.S. Cl.
CPC ............. *A61B 5/316* (2021.01); *A61B 5/364* (2021.01); *A61B 5/366* (2021.01); *A61B 5/339* (2021.01)

(58) Field of Classification Search
CPC ......... A61B 5/316; A61B 5/364; A61B 5/366; A61B 5/339
See application file for complete search history.

(56) References Cited

U.S. PATENT DOCUMENTS

2011/0125041 A1* 5/2011 Fischell ................ A61B 5/364
600/515

* cited by examiner

*Primary Examiner* — George Manuel
(74) *Attorney, Agent, or Firm* — John R. Kasha; Kelly L. Kasha; Kasha Law LLC

(57) ABSTRACT

Electrical impulses are received from a beating heart. The electrical impulses are converted to an ECG waveform. The ECG waveform is converted to a frequency domain waveform, which, in turn, is separated into two or more different frequency domain waveforms, which, in turn, are converted into a plurality of time domain cardiac electrophysiological subwaveforms and discontinuity points between these subwaveforms. The plurality of subwaveforms and discontinuity points are compared to a database of subwaveforms and discontinuity points for normal and abnormal patients or to a set of rules developed from the database. A bundle branches (BB) to J-Point (BB-J) interval is identified from the plurality of subwaveforms and discontinuity points based on the comparison. The ECG waveform with the BB-J interval annotated is displayed.

20 Claims, 25 Drawing Sheets

Related U.S. Application Data which is a continuation of application No. PCT/US2015/020828, filed on Mar. 16, 2015.

(60) Provisional application No. 62/742,477, filed on Oct. 8, 2018, provisional application No. 62/727,028, filed on Sep. 5, 2018, provisional application No. 62/701,841, filed on Jul. 23, 2018, provisional application No. 62/571,180, filed on Oct. 11, 2017, provisional application No. 62/551,759, filed on Aug. 29, 2017, provisional application No. 62/546,461, filed on Aug. 16, 2017, provisional application No. 62/489,540, filed on Apr. 25, 2017, provisional application No. 62/463,662, filed on Feb. 26, 2017, provisional application No. 62/271,704, filed on Dec. 28, 2015, provisional application No. 62/271,699, filed on Dec. 28, 2015, provisional application No. 62/017,185, filed on Jun. 25, 2014, provisional application No. 62/008,435, filed on Jun. 5, 2014.

| Parameter | Standard Values | Test Data |
|---|---|---|
| P-P interval | 600~1,000 ms | 784 ms |
| R-R interval | 600~1,000 ms | 784 ms |
| T-T interval | 600~1,000 ms | 784 ms |
| P-R interval | 120~200 ms | 144 ms |
| PA interval | 25~35 ms | 30 ms |
| AH interval | 60~110 ms | 66 ms |
| HV interval | 35~55 ms | 47 ms |
| QRS complex | < 120 ms | 82 ms |
| ST segment | < T segment | 95 ms |
| T segment | > ST segment | 207 ms |
| S-T interval | < 380 ms | 304 ms |
| P-J interval | < 270 ms | 227 ms |
| J-T interval | < 380 ms | 304 ms |
| Q-T interval | < 340~440 ms | 374 ms |
| T-Q interval | > 340~440 ms | 429 ms |
| j-R segment | < 60 ms | 40 ms |
| R-j segment | < 60 ms | 43 ms |
| J-Tp segment |  | 210 ms |
| Tp-Te segment |  | 93 ms |
| BB-J interval | < 150 ms | 100 ms |
| BB-ST interval | < 250 ms | 177 ms |

FIG. 23

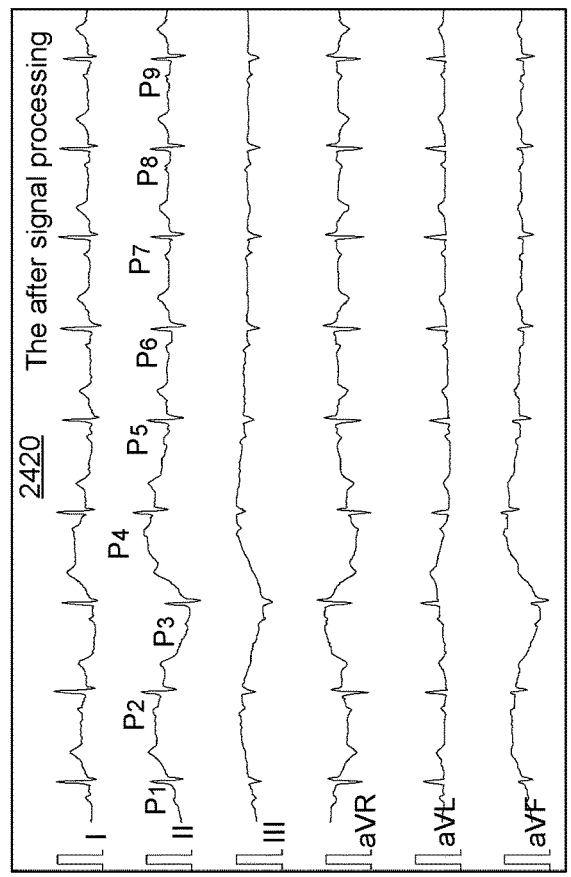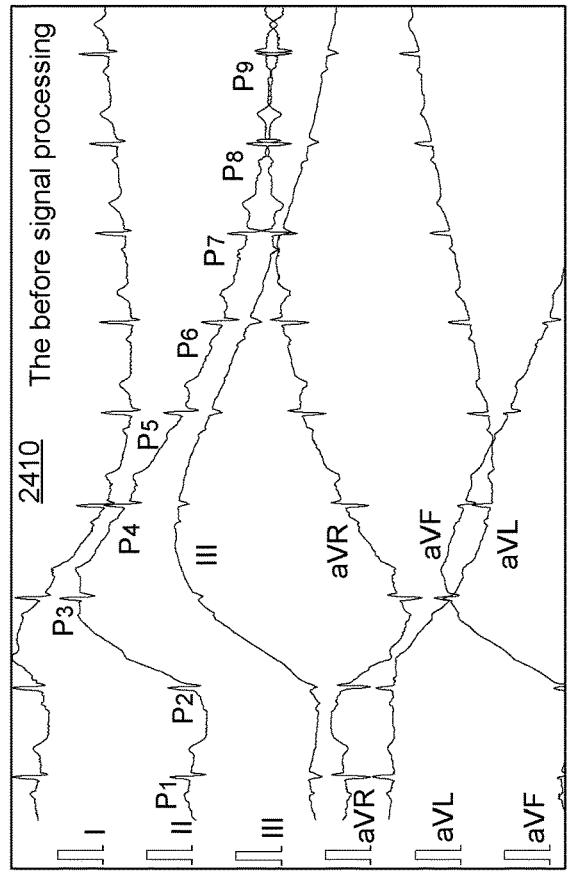
FIG. 24

GENERATION OF VITAL SIGN MONITORING

CROSS-REFERENCE TO RELATED APPLICATION

This application is a continuation in part of U.S. patent application Ser. No. 16/561,304, filed Sep. 5, 2019, which is a continuation in part of U.S. patent application Ser. No. 16/157,178, filed Oct. 11, 2018, which is a continuation in part of U.S. patent application Ser. No. 16/114,025, filed Aug. 27, 2018, which is a continuation in part of U.S. patent application Ser. No. 15/998,487, filed Aug. 16, 2018, which is a continuation in part of U.S. patent application Ser. No. 15/961,952, filed Apr. 25, 2018, now U.S. Pat. No. 10,092,201, which is a continuation in part of U.S. patent application Ser. No. 15/904,543, filed Feb. 26, 2018, now U.S. Pat. No. 10,085,663, which is a continuation in part of U.S. patent application Ser. No. 15/393,135, filed Dec. 28, 2016, now U.S. Pat. No. 9,999,364, which is a continuation in part of U.S. patent application Ser. No. 14/749,697, filed Jun. 25, 2015, now U.S. Pat. No. 9,538,930 (hereinafter the "'930 Patent"), which is a continuation in part of U.S. patent application Ser. No. 14/662,996, filed Mar. 19, 2015, now U.S. Pat. No. 9,339,204 (hereinafter the "'204 Patent"), which is a continuation of PCT Application No. PCT/US15/20828, filed Mar. 16, 2015, which claims the benefit of U.S. Provisional Patent Application Ser. No. 62/008,435, filed Jun. 5, 2014; this application also claims the benefit of U.S. Provisional Patent Application Ser. No. 62/742,477, filed Oct. 8, 2018, this application also claims the benefit of U.S. Provisional Patent Application Ser. No. 62/727,028, filed Sep. 5, 2018; U.S. patent application Ser. No. 16/157,178 claims the benefit of U.S. Provisional Patent Application Ser. No. 62/571,180, filed Oct. 11, 2017 and U.S. Provisional Patent Application Ser. No. 62/701,841, filed Jul. 23, 2018; U.S. patent application Ser. No. 16/114,025 claims the benefit of U.S. Provisional Patent Application Ser. No. 62/551,759, filed Aug. 29, 2017; U.S. patent application Ser. No. 15/998,487 claims the benefit of U.S. Provisional Patent Application Ser. No. 62/546,461, filed Aug. 16, 2018; U.S. patent application Ser. No. 15/961,952 claims the benefit of U.S. Provisional Patent Application Ser. No. 62/489,540, filed Apr. 25, 2017; U.S. patent application Ser. No. 15/904,543 claims the benefit of U.S. Provisional Patent Application Ser. No. 62/463,662, filed Feb. 26, 2017; U.S. Patent Application Serial No. application Ser. No. 15/393,135 claims the benefit of U.S. Provisional Patent Application Ser. No. 62/271,704, filed Dec. 28, 2015, and U.S. Provisional Patent Application Ser. No. 62/271,699, filed Dec. 28, 2015; and U.S. patent application Ser. No. 14/749,697 claims the benefit of U.S. Provisional Patent Application Ser. No. 62/017,185, filed Jun. 25, 2014, the content of all of which is incorporated by reference herein in their entireties.

INTRODUCTION

The teachings herein relate to vital sign monitoring using an automated electrocardiography (ECG) analysis system. More particularly, the teachings herein relate to systems and methods for displaying and measuring intervals and segments of an ECG waveform during measurement of the ECG waveform. These systems and methods use the harmonic signals of a conventional ECG waveform and previously recorded data from normal and abnormal patients or rules developed from the previously recorded data to identify a bundle branches (BB) to J-Point (BB-J) interval of an ECG waveform.

The systems and methods herein can be performed in conjunction with a processor, controller, or computer system, such as the computer system of FIG. 1.

BACKGROUND

Traditional Vital Sign Monitoring

Since its invention in 1903, the ECG device has not significantly changed. Abnormalities are sometimes displayed as normal and normal results are sometimes displayed as abnormal, making it almost impossible for doctors and nurses to correctly recognize and diagnose disease. The main reason for this ambiguity is the abstract self-similarity of the existing ECG waveform.

The ECG waveform is the most important parameter of Vital Sign Monitoring. Blood Pressure (NIBP) and Oxygen Saturation (SpO2) are secondary parameters. Death is mainly caused by cardiac changes within the heart, even when there is no disease evident. The cardiac information changes quickly from physiological to pathological. However, the current Vital Signs Monitor is only a warning device after the occurrence of critical events.

Also, many myocardial ischemia events do not even trigger an alarm. Myocardial infarction does not trigger an alarm. Heart failure does not trigger an alarm. Serious conduction block does not trigger an alarm. Serious coronary heart disease does not trigger an alarm. AMI, ACS, and so on, all do not trigger an alarm in advance, leading to risk factors that lead to death when the alarm is finally triggered. This represents an imperative on the traditional vital sign monitoring of cardiac monitor.

In current Vital Sign Monitoring, when patients appear to show signs of Ventricular Tachycardia (VT), Ventricular Fibrillation (VF) or acute cardiac events, it is already too late. The existing ECG detection rate of coronary heart disease is only 17~25%. Only half of patients with acute myocardial infarction with impairment greater than 70% can be detected. This is because a traditional ECG device does not display ST segment changes in elevation or descent accurately. In the early stages of cardiac ischemia, if immediate action is not taken, the monitor loses its basic functions.

As a result, there is a need for Vital Sign Monitoring ECG systems and methods that provide automatic detection of possible disease and no longer simply act as an alarm device after the occurrence of critical events.

ECG Quantitative Problem

Since the development of ECG, the electrophysiological signal separation of specific time periods of cardiac self-conduction system within the P wave, the QRS complex and the T wave has never been achieved. There is standardized data available in cardiac science, but such quantitative data has never been used in ECG for many reasons. Conventionally, only the character of an ECG waveform is read. As a result, only qualitative information is provided in clinical applications.

ECG is a noninvasive electrophysiological technology. It is able to scan and record cardiac electrical conduction signals. It is the only tracing image of cardiac "bioelectric conduction", which is the character marker of the life of a heart. However, in the medical field, ECG is only a morphological technique, and the target of its reading, analyzing and determining is waveform character. It is a qualitative technology that does not have quantitative data, which is due to the ECG waveform being associated with deformation and instability. The standard measuring points frequently disappear, hide, overlap and shift. Consequently, they are frequently not shown in ECG, and thus cannot be used for making a determination.

Moreover, conventional ECG cannot measure all digital parameters. The established standards cannot be applied clinically, and cannot be measured. As a result, ECG is unable to achieve a data-based quantitative application. Hence, to date, ECG is still a qualitative application. The foregoing is the reason for which ECG is deemed as a technology that needs experience. However, it is noted that such experience needs to be accumulated from a great number of cases with incorrect diagnosis.

The heart is the most important organ in human body. In addition to heart diseases, a variety of other diseases may also cause abnormalities in heart. Hence, not only cardiologists, but also all doctors in other departments need to read ECG. However, the morphological character changes in ECG cause difficulties for doctors to read ECG. Hence, the issue of how to use the ECG data has confused clinical practices for many years. In traditional ECG, diagnosis of diseases is still made according to morphological character changes in waveforms.

As a result, systems and methods are needed to add quantitative scientific indicators to ECG. Such systems and methods are needed to allow doctors to understand and utilize the knowledge saved in traditional ECG, as well as to reduce learning difficulties, reduce guesses in case diagnosis, reduce misjudgment rate, and improve reliability, diagnosis rate and accuracy, whenever waveform character changes.

ECG Accuracy Problem

Since the first ECG instrument was invented in 1903, its accuracy rate for diagnosis has always been a problem in clinical applications. For people with abnormal conditions, ECG waveform variations are not the same for the same person and are not completely identical even for the same disease. They are at most self-similar. Self-similarly, for example, refers to an object having a shape that is similar to the shape of one of its parts. As a result, ECG science is one of the most complicated disciplines in medicine.

It can be seen from numerous signal processing methods that, during a lifetime, each beat of a person's heart has different specific signal variation, and the difference is significant. However, generally one is unable to observe this from a conventional linear ECG waveform with the naked eye.

Since computers started to be widely used in ECG analysis the 1970s, people have been consistently exploring, searching, and studying how to automate ECG analysis and diagnosis. In the past half a century, thousands of scholars have made efforts in studying algorithms, exploring pattern recognition, and applying those in ECG mapping and automatic diagnosis.

However, wide clinical use of such systems has yet to be achieved. There are at least three technical reasons for this.

1. The ECG waveform is morphological, and generally no consistent mapping points can be found. In other words, the information in the ECG waveform is conveyed through its structure or form. Also, the waveform is abstractly self-similar. In particular, there is no rule for abnormal variations, the time axis signals interfere with each other on left and right sides of as well as above the x-axis, non-linear variations are invisible, and the same disease may have hundreds of millions of variations, but they are not clearly displayed on the ECG waveform. As a result, all ECG parameters are, in general, not accurate, and it is almost impossible to measure these parameters after the waveform changes. Therefore, the highest accuracy of automatic diagnosis by existing ECG software reaches around 38%. Also, this accuracy is only achieved for simple ECG waveform variations and not for many complex waveforms. This is because no mapping point can be found due to the loss or disappearance or deformation of the P-QRS-T waveform.

2. The second reason systems for automated ECG analysis and diagnosis have not been adopted clinically is related to how a conventional ECG waveform has been measured. As described in the '204 Patent and below, the conventional ECG waveform is a single time domain waveform that represents a combination of many different frequency domain signals from different parts of the heart muscle. As a result, information specific to these different parts of the heart muscle are generally lost. In addition, the conventional ECG waveform is a linear waveform, while the heart is a nonlinear system, and the vast majority of variations as a result of abnormality are nonlinear.

3. The third reason systems for automated ECG analysis and diagnosis have not been adopted clinically is related to the high number of false positives found in normal and abnormal populations. For example, in many cases, conventional ECG waveforms show abnormal results in tests of normal people and also show normal results in tests of abnormal people, which makes it extremely difficult for clinical reading and understanding and makes it impossible to determine whether a result is normal or abnormal.

However, the heart is an electrified organ, and there is no doubt that the electrophysiological responses of a heart organ are the fastest and most sensitive measurements to diagnose heart problems. ECG remains one of the most extensively used clinical tools used at present along with blood tests and imaging, despite the lack of accurate systems for automated ECG analysis and diagnosis. As a result, there is a significant need for such systems.

Recent advancements have addressed one of the three technical problems. This is the conventional ECG waveform measurement problem. As described in the '204 Patent and below, an ECG device has been developed that uses signal processing to detect one or more subwaveforms within the P, Q, R, S, T, U, and J waveforms of a conventional ECG waveform and/or within the intervals between the P, Q, R, S, T, U, and J waveforms of a conventional ECG waveform. In other words, the device of the '204 Patent can provide information (subwaveforms) about different frequency domain signals from different parts of the heart muscle. A waveform displaying these subwaveforms is referred to as a saah ECG waveform, for example. In FIG. 30, described below, portions of a saah ECG waveform 3030 and a conventional or traditional ECG waveform 3040 are compared. FIG. 30 shows that saah ECG waveform 3030 relates ECG signals more closely to the anatomy of self-conducting system 3020 than traditional ECG waveform 3040.

As described in the '930 Patent and below, one way the different frequency domain signals from different parts of the heart muscle can be measured is through multi-domain ECG. In multi-domain ECG heart signals are measured using different frequency bands. These multi-domain ECG heart signals can be displayed in one diagram as an electrophysiocardiogram (EPCG) waveform. FIG. 32 shows EPCG waveforms before and after percutaneous coronary intervention (PCI), for example.

As a result of the systems of the '204 Patent and the '930 Patent, the technical problem of measuring the different frequency domain signals from different parts of the heart muscle has been addressed.

ECG Parameter Measurement Problem

The heart beats day and night from the first day of a human life to the last day of life. In a whole life, the heart beats about 2.5 billion to 3 billion times. In this regard, it could be calculated that the heart each time pumps 80 ml blood. Accordingly, based on the fact that the heart beats about 70 times per minute on average, the heart hence pumps 8,000 liters of blood per day, which is equivalent to the volume of 40 barrels of gasoline, and the total weight would be 8 tons. Therefore, the heart pumps 3,000 tons of blood per year. If a person lives for 80 years, the number will reach 240,000 tons. It is noted that after the age of 60 years old, a person has a 45% chance of having the condition of arrhythmia, and about half of those cases become life threatening. According to a variety of different scientific predictions, some scientists believe that it is reasonable to predict that the average lifespan of a person is about 80 years old.

The heart is a charged elastic mucus organ, so an ECG instrument is the only instrument that is able to scan and record the physiological and pathological signs of the cardiac electrophysiology (heart ultrasound provides hemodynamic data, CT & MIR provide histological imaging data). ECG provides electrophysiological signals, in particular noninvasive electrophysiological data. It is able to scan and record cardiac electrical conduction signals. By far, it is the only tool that can record the scanning image of "bioelectric conduction," the identifier of a living heart.

On the other hand, however, in the medical field, ECG is also only a morphological signal. It needs to be read and analyzed to determine its various waveforms. In this regard, it is an area that highly relies on a practitioner's experience. In the history of ECG, there are many data-based parameter gold standards, such as P-R interval, Q-T interval, ST segment, QRS complex, P-J interval, J-T interval, VAT.

However, due to the fact that ECG waveforms are prone to certain issues such as deformation, instability, standard point loss, and so on, conventional ECG instruments are unable to accurately measure these ECG parameters. As a result, many established standards cannot be applied in clinical practice.

Furthermore, as for the data measured manually, a very small variation can result in a difference of tens of milliseconds. Clinically, only simple standards can be used at present, such as: HR, RR interval, PP interval. As a result, only a few very simple standards can be used in current clinical practice, including HR, RR interval, PP interval, etc.

As described above, the ECG systems of the '204 Patent and the '930 Patent have addressed the technical problem of accurately measuring the different frequency domain signals from different parts of the heart muscle.

Additional systems and methods, however, are needed to accurately measure ECG parameters such as the P-R interval, Q-T interval, ST segment, QRS complex, P-J interval, J-T interval, and VAT so that these standards can be used in clinical practice.

ECG History

Electrical signals produced by a human heart were observed through electrodes attached to a patient's skin as early as 1879. Between 1897 and 1911 various methods were used to detect these electrical signals and record a heartbeat in real-time. In 1924, Willem Einthoven was awarded the Nobel Prize in medicine for identifying the various waveforms of a heartbeat and assigning the letters P, Q, R, S, T, U, and J to these waveforms. Since the early 1900s, the equipment used for electrocardiography (ECG or EKG) has changed. However, the basic waveforms detected and analyzed have not changed.

An ECG device detects electrical impulses or changes in the electrical potential between two electrodes attached to the skin of a patient as the heart muscle contracts or beats. Electrically, the contraction of the heart is caused by depolarization and repolarization of various parts of the heart muscle. Initially, or at rest, the muscle cells of the heart have a negative charge. In order to cause them to contract, they receive an influx of positive ions $Na^+$ and $Ca^{++}$. This influx of positive ions is called depolarization. The return of negative ions to bring the heart back to a resting state is called repolarization. Depolarization and repolarization of the heart affect different parts of the heart over time giving rise to the P, Q, R, S, T, U, and J waveforms.

FIG. 2 is an exemplary plot 200 of the P, Q, R, S, and T waveforms of a conventional ECG waveform of a heartbeat from a conventional ECG device. The P, Q, R, S, and T waveforms represent electrical conduction through a heart muscle. P waveform 210 represents the propagation of depolarization from the sinoatrial node, to the right and left atriums, and to the atrioventricular node. The sinoatrial node is also referred to as the sinus node, SA node, or SAN. The atrioventricular node is also referred to as the AV node or AVN. The right atrium is also referred to as the RA, and the left atrium is also referred to as the LA.

FIG. 3 is an exemplary diagram 300 of the depolarization of the muscle tissue of a heart that produces P waveform 210 of FIG. 2 as detected by a conventional ECG device. P waveform 210 of FIG. 2 is produced as depolarization propagates from SAN 310 to AVN 340 in FIG. 3. As depolarization propagates from SAN 310 to AVN 340, it also spreads from RA 320 to LA 340. P waveform 210 of FIG. 2 typically has a duration of 80 ms, for example.

PR segment 220 of FIG. 2 represents the propagation of depolarization from the AVN to the Bundle of His, and then to the Bundle Branches. PR segment 230 may also include depolarization to the Purkinje fibers of the inner ventricular walls. The Bundle of His is also referred to as the His Bundle or His. The Bundle Branches include the right bundle branches (RBB) and the left bundle branches (LBB). As shown in FIG. 2, in a conventional ECG, PR segment 220 shows up as a flat line or waveform with no amplitude.

FIG. 4 is an exemplary diagram 400 of the depolarization of the muscle tissue of a heart that produces PR segment 220 of FIG. 2 as detected by a conventional ECG device. PR segment 220 of FIG. 2 is produced as depolarization propagates from AVN 340 to His 450 and then to Bundle Branches 460 that include RBB 461 and LBB 462. PR segment 220 of FIG. 2 typically has a duration of between 50 and 120 ms, for example.

Waveforms Q 230, R 240, and S 250 of FIG. 2 form the QRS complex. The QRS complex represents the propagation of depolarization through the right and left ventricles. The right ventricle is also referred to as RV, and the left ventricle is referred to as LV.

FIG. 5 is an exemplary diagram 500 of the depolarization of the muscle tissue of a heart that produces Q waveform 230, R waveform 240, and S waveform 250 of FIG. 2 as detected by a conventional ECG device. Waveforms Q 230, R 240, and S 250 of FIG. 2 produced as depolarization propagates from Bundle Branches 460 through RV 571 and LV 572. RV 571 and LV 572 have the largest muscle mass in the heart. The QRS complex formed by waveforms Q 230, R 240, and S 250 of FIG. 2 typically has a duration of between 80 and 100 ms, for example.

ST segment 260 of FIG. 2 represents the period during which the ventricles remain depolarized and contracted. As shown in FIG. 2, in a conventional ECG, ST segment 260 shows up as a flat line or waveform with no amplitude. ST segment 260 typically has a duration of between 80 and 120 ms, for example.

The point in FIG. 2 at which the QRS complex ends and ST segment 260 begins is called J point 255. A J waveform (not shown) can sometimes appear as an elevated J point at J point 255 or as a secondary R waveform. A J waveform is usually characteristic of a specific disease. The J waveform is also referred to as the Osborn wave, camel-hump sign, late delta wave, hathook junction, hypothermic wave, prominent J wave, K wave, H wave or current of injury.

T waveform 270 of FIG. 2 represents the repolarization or recovery of the ventricles. T waveform 270 typically has a duration of 160 ms, for example. The interval between the Q and T waveforms is referred to as the QT interval.

FIG. 6 is an exemplary diagram 600 of the repolarization of the muscle tissue of a heart that produces T waveform 270 of FIG. 2 as detected by a conventional ECG device. As shown in FIG. 6, RV 571 and LV 572 are repolarized.

Not shown in FIG. 2 is the U waveform. The U waveform sometimes appears after the T waveform. The U waveform is thought to represent repolarization of the interventricular septum, the papillary muscles, or the Purkinje fibers.

As shown in FIGS. 3 through 6, as a heart beats, electrical signals flow through all the different muscle tissues of the heart. As shown in FIG. 2, for the last 100 years conventional ECG devices have been able to detect some of these signals in the form of the P, Q, R, S, T, U, and J waveforms. These waveforms have aided in the diagnosis and treatment of many heart problems. Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

Artificial Intelligence

Artificial Intelligence (AI) generally refers to languages, algorithms, and operating systems that relate to how a computer system can carry out tasks that were previously only completed by relying on human intelligence. It is a general term and often does not include implementation or application. The definition of AI has evolved over time, however, and this phenomenon is referred to as the "AI effect." The AI effect can be summarized as the prescription that "AI intends to complete a collection of all tasks that cannot be implemented without relying on human intelligence at the present." In the 1940s and 1950s, a group of scientists from different fields (mathematics, psychology, engineering, economics and politics) began to explore the possibility of manufacturing an artificial brain. In 1956, AI was established as a discipline. The organizers of the 1956 Dartmouth Artificial Intelligence Conference were Marvin Minsky, John McCarthy, and two other senior scientists, Claude Shannon and Nathan Rochester, with the latter coming from IBM. At the 1956 Dartmouth Artificial Intelligence Conference, the name and tasks of AI were determined, and at the same time, initial achievements and the earliest group of researchers appeared. As a result, this event has been extensively acknowledged as a sign of the birth of AI. It is clear that AI is now a technological field, a second revolution since the invention of the computer, and a certain trend in the future. It is being applied in all industries, exists everywhere, and is used on almost everything on the earth. In the medical field, AI is now used in the following: medical imaging, sensor-based data analysis, conversion of bioinformatics, and development of public health policies. AI is also used in the clinical applications. These applications include cancer treatment: recognition of mitosis of cancerous tumor cells, identification of disease types and degrees of aggravation, shortening chemotherapy time, and mitigating damage caused by chemotherapy for cancer patients. These applications also include ophthalmological diagnosis: recognition of early signs of eye disease, such as senile macular degeneration, and diabetic retinopathy and surgical treatment: AI surgical robots, etc. Google has also formed a team called DeepMind Health, which cooperated with the Imperial College London and the Royal Free Hospital in London, UK. They released a mobile application called Streams, and medical professionals can use Streams to observe treatment results in a faster manner. Overall, in the medical field, the AI system can be used on any job that previously required human thinking.

BRIEF DESCRIPTION OF THE DRAWINGS

FIG. 23 is an exemplary table showing the timing parameter values of the ECG waveform in FIG. 22, including new timing parameter values, in accordance with various embodiments.

FIG. 24 is an exemplary diagram showing how heart signal drift is filtered, in accordance with various embodiments.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DETAILED DESCRIPTION

Computer-Implemented System

Figure 1:
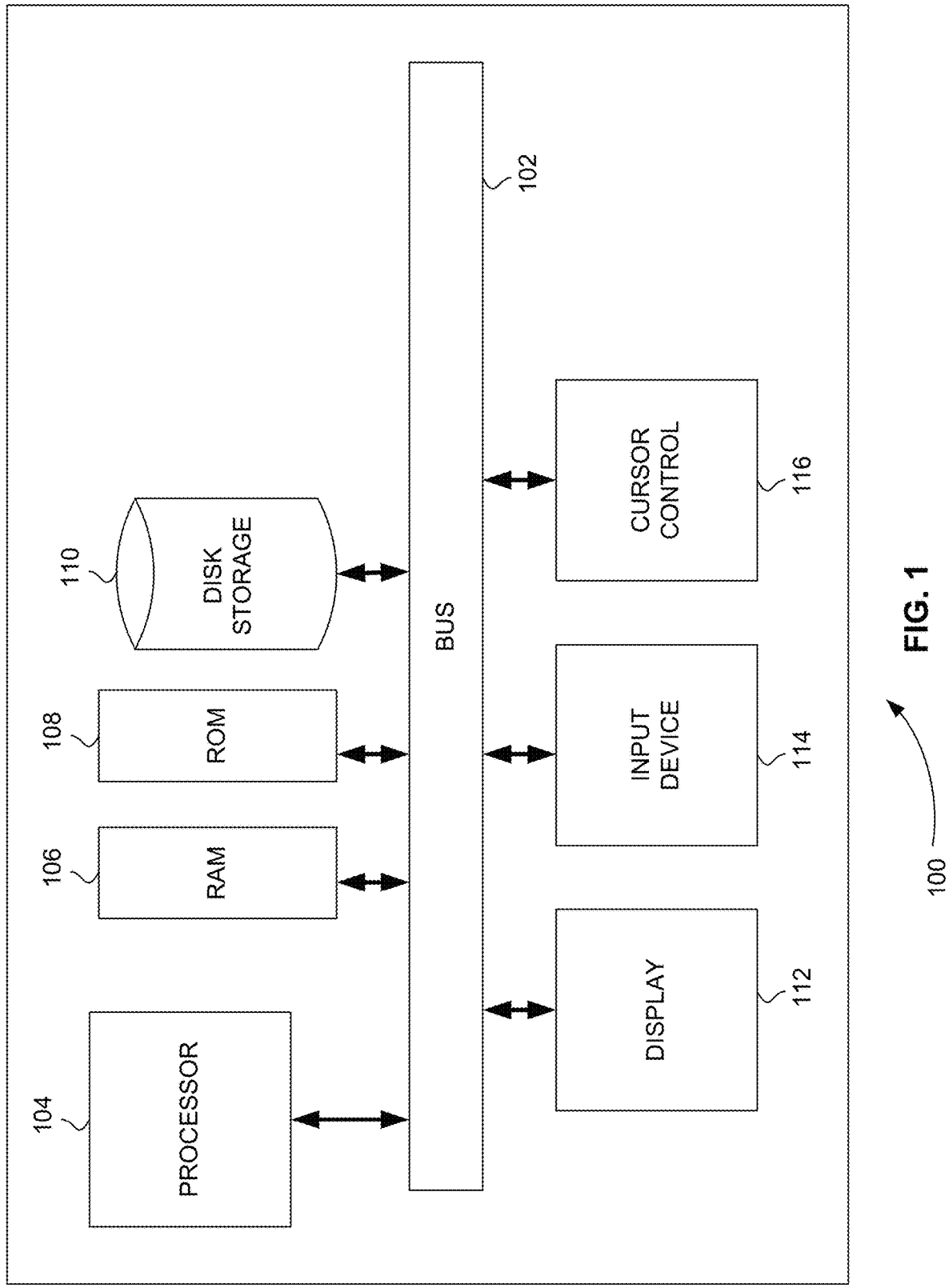
FIG. 1 is a block diagram that illustrates a computer system, in accordance with various embodiments.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random-access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus, implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer-readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Subwaveform Detection of the P, Q, R, S, T, U, and J Waveforms

As described above, electrical signals flow through all the different muscle tissues of the heart. For the last 100 years, conventional ECG devices have been able to detect some of these signals in the form of the P, Q, R, S, T, U, and J waveforms. These waveforms have aided in the diagnosis and treatment of many heart problems.

Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

In various embodiments, additional information is obtained from the electrical signals produced by a heart through signal processing. More specifically, signal processing is added to an ECG device in order to detect more information from the electrical signals that flow through all the different muscle tissues of the heart as it is beating.

Figure 7:
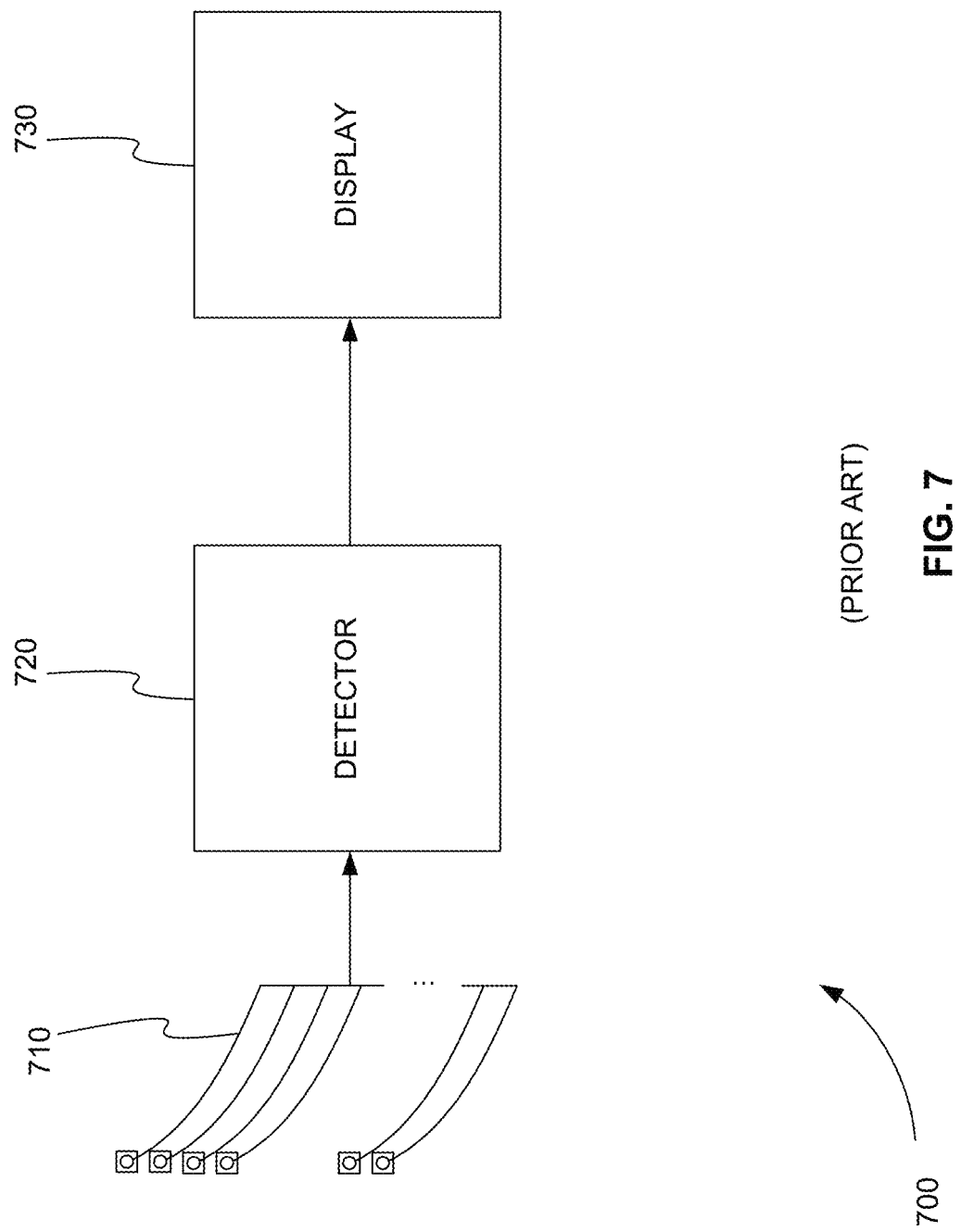
FIG. 7 is a block diagram of a conventional ECG device.

FIG. 7 is a block diagram 700 of a conventional ECG device. The conventional ECG device includes two or more leads or electrodes 710. Electrodes 710 are typically attached to the skin of a patient. Electrical signals produced by a beating heart are detected between pairs of electrodes 710. Because the heart is three-dimensional, electrodes are attached at different locations on a body to detect signals at different corresponding locations or angles from the heart. In other words, the electrodes are placed on a body to partially surround the heart. One typical type of ECG includes 12 electrodes, for example.

A voltage signal is detected between two electrodes 710 by detector 720. Detector 720 also typically amplifies the voltage signal. Detector 720 can also convert the voltage signal to a digital voltage signal using an analog to digital converter (A/D).

Detector 720 provides the detected and amplified voltage signal from each pair of electrodes 710 to display 730. Display 730 can be an electronic display device including, but not limited to, a cathode ray tube (CRT) device, light emitting diode (LED) device, or Liquid crystal display (LCD) device. Display 730 can also be a printer device. Additionally, display 730 can include a memory device to record detected signals. The memory device can be, but is not limited to, a volatile electronic memory, such as random access memory (RAM), a non-volatile electronic memory, such as electrically erasable programmable read-only memory (EEPROM or Flash memory), or a magnetic hard drive.

Figure 2:
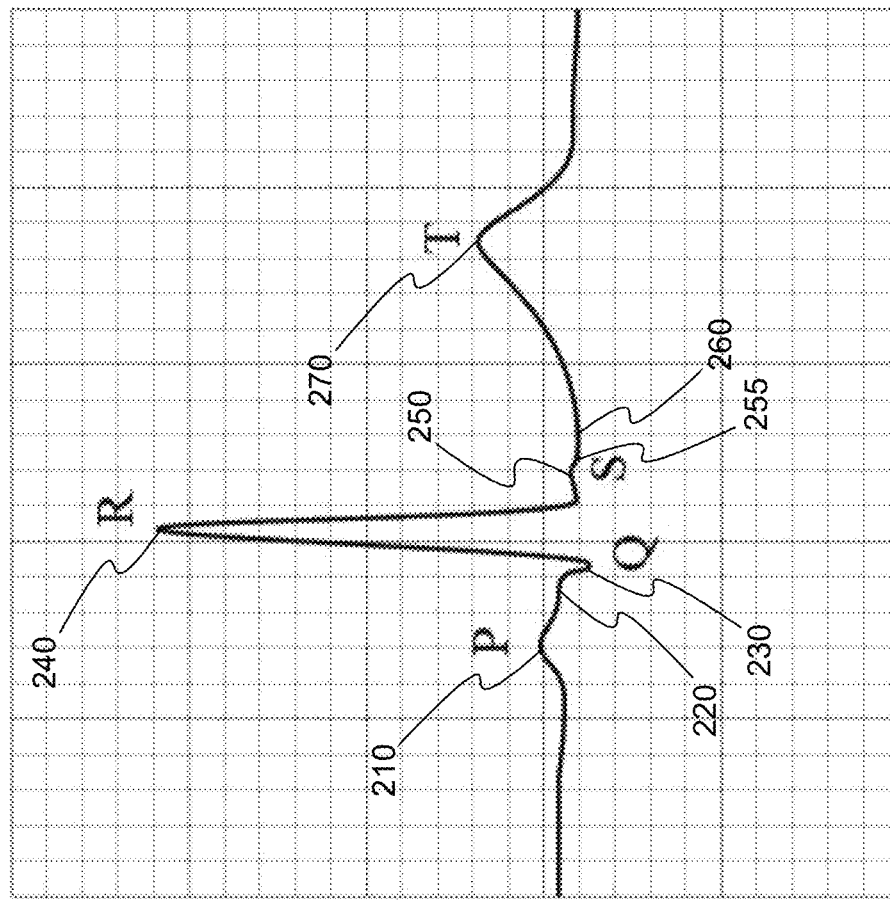
FIG. 2 is an exemplary plot of the P, Q, R, S, and T waveforms of a conventional electrocardiography (ECG) waveform of a heartbeat from a conventional ECG device.
Figure 3:
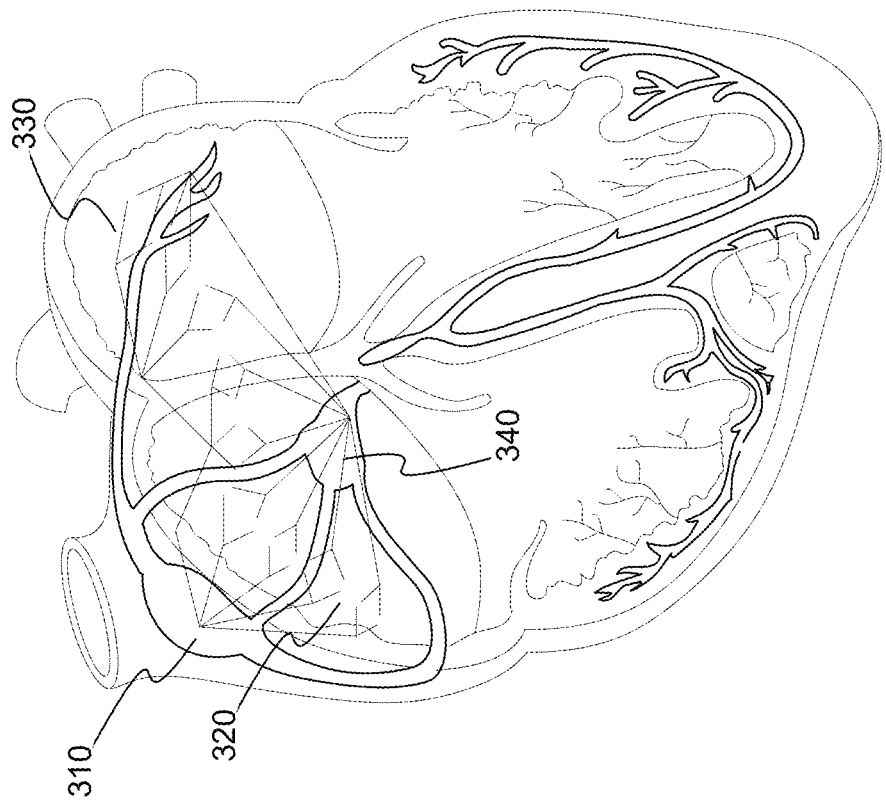
FIG. 3 is an exemplary diagram of the depolarization of the muscle tissue of a heart that produces the P waveform of FIG. 2 as detected by a conventional ECG device.
Figure 4:
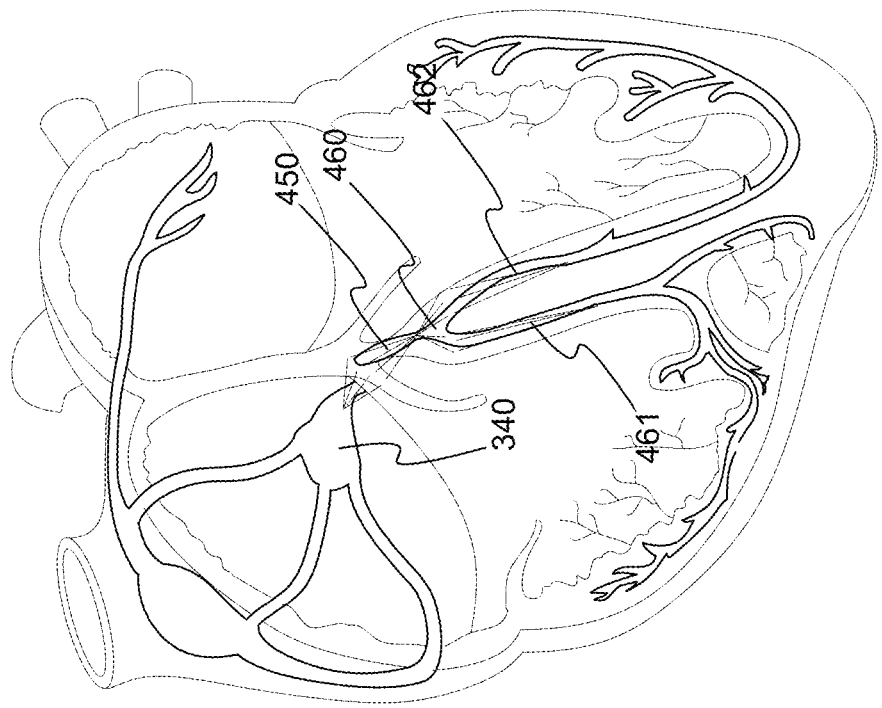
FIG. 4 is an exemplary diagram of the depolarization of the muscle tissue of a heart that produces the PR segment of FIG. 2 as detected by a conventional ECG device.
Figure 5:
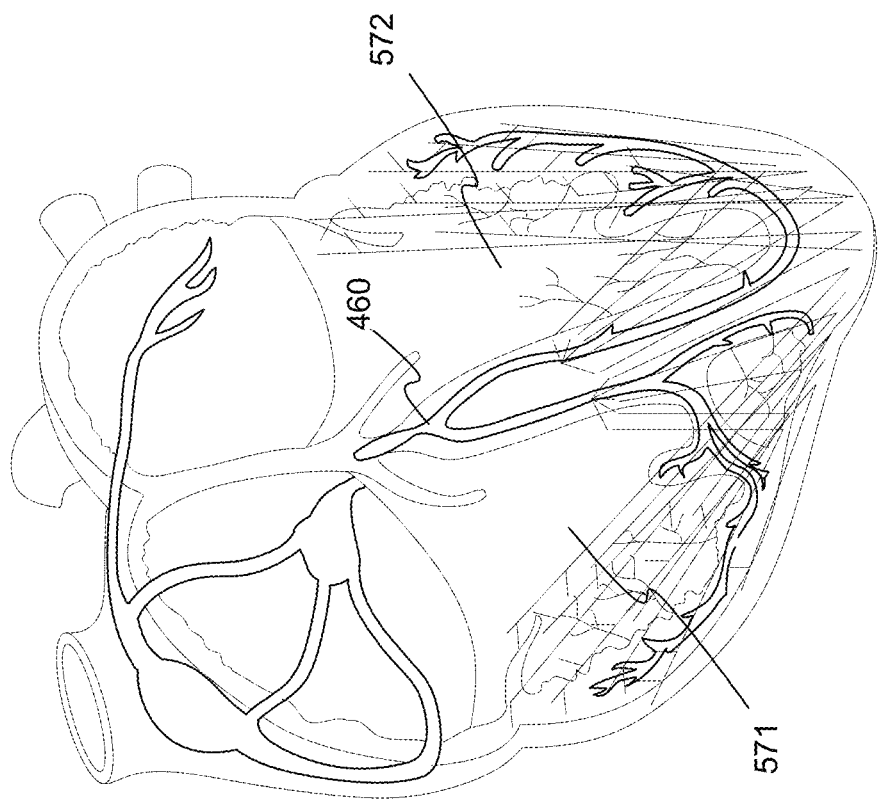
FIG. 5 is an exemplary diagram of the depolarization of the muscle tissue of a heart that produces the Q waveform, the R waveform, and the S waveform of FIG. 2 as detected by a conventional ECG device.
Figure 6:
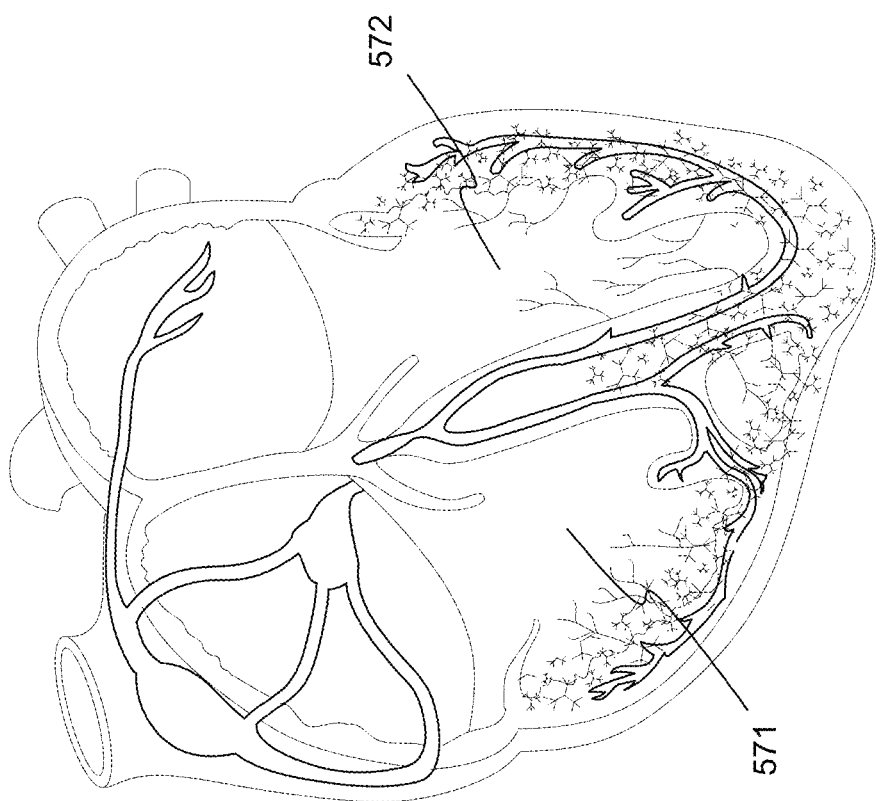
FIG. 6 is an exemplary diagram of the repolarization of the muscle tissue of a heart that produces the T waveform of FIG. 2 as detected by a conventional ECG device.

Display 730 displays a continuous loop of the detected P, Q, R, S, T, U, and J waveforms as shown in FIG. 2 for each pair of electrodes 710. Modern ECG devices can also include a processor (not shown), such as the processor shown in FIG. 1, to analyze the P, Q, R, S, T, U, and J waveforms. For example, the processor can calculate the time periods of the P, Q, R, S, T, U, and J waveforms and the times between the P, Q, R, S, T, U, and J waveforms. The processor can also compare this timing information to stored normal information. Based on the comparison, the processor can determine differences from the normal data. All information calculated by the processor can also be displayed on display 730.

Figure 8:
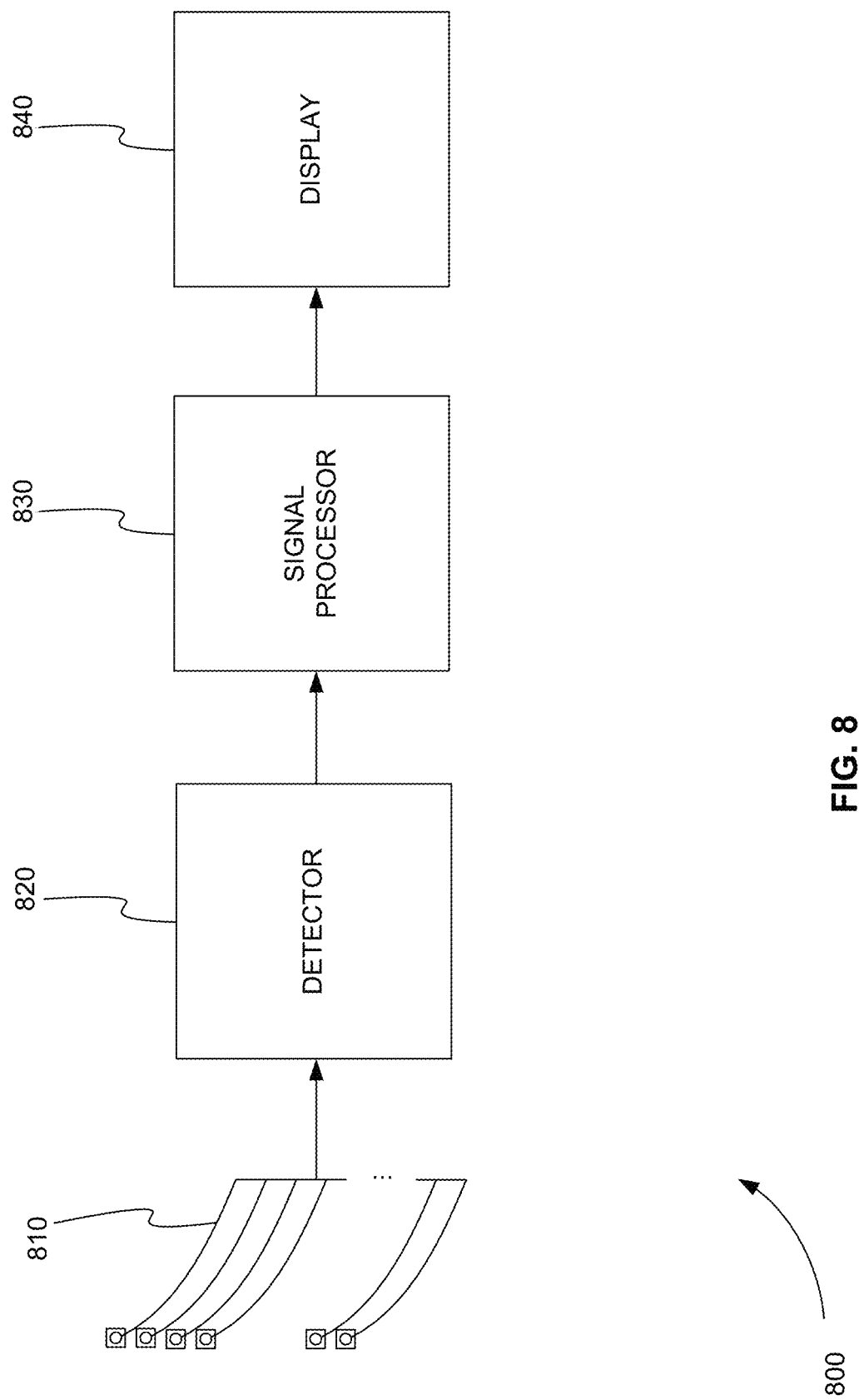
FIG. 8 is a block diagram of an ECG device for detecting more information from the electrical signals that flow through all the different muscle tissues of the heart as it is beating, in accordance with various embodiments.

FIG. 8 is a block diagram 800 of an ECG device for detecting more information from the electrical signals that flow through all the different muscle tissues of the heart as it is beating, in accordance with various embodiments. Electrodes 810 are attached to the skin of a patient, for example. Electrical signals produced by a beating heart are detected between pairs of electrodes 810.

A voltage signal is detected between two electrodes 810 by detector 820. Detector 820 also amplifies the voltage signal. Detector 820 also converts the voltage signal to a digital voltage signal using an analog to digital converter (A/D).

Detector 820 provides the detected and amplified voltage signal from each pair of electrodes 810 to signal processor 830. Detector 820 can also provide the detected and amplified voltage signal from each pair of electrodes 810 directly to display device 840 to display the conventional P, Q, R, S, T, U, and J waveforms.

Signal processor 830 detects or calculates one or more subwaveforms within and/or in the interval between the P, Q, R, S, T, U, and J waveforms of each detected and amplified voltage signal. A waveform is a shape or form of a signal. A subwaveform is shape or form of a signal that is within or part of another signal.

Signal processor 830 can be a separate electronic device that can include, but is not limited to, an application specific integrated circuit (ASIC), a field programmable gate array (FPGA), or a general-purpose processor. Signal processor 830 can be software implemented on another processor of the ECG device, such as a processor of display device 840. Signal processor 830 can also be a remote server that receives the detected and amplified voltage signal from detector 820, detects or calculates one or more subwaveforms within and/or in the interval between the P, Q, R, S, T, U, and J waveforms, and sends the detected and amplified voltage signal and the one or more subwaveforms to display device 840.

Signal processor 830 sends one or more subwaveforms of each detected and amplified voltage signal to display device 840. Signal processor 830 can also calculate and send to the display device 840 the time periods of the one or more subwaveforms, the times between the one or more subwaveforms, and the times of the one or more subwaveforms in relation to the P, Q, R, S, T, U, and J waveforms and or the intervals between the P, Q, R, S, T, U, and J waveforms. Signal processor 830 can also compare this timing information to stored normal timing information. Based on the comparison, signal processor 830 can determine differences from the normal data and send this difference information and any of the timing information to display device 840.

Display device 840 displays a continuous loop of the one or more subwaveforms for each pair of electrodes 810. Display device 840 can also display part or all of the conventional P, Q, R, S, T, U, and J waveforms for comparison with the one or more subwaveforms. Like display 730 of FIG. 7, display device 840 of FIG. 8 can be an electronic display device, a printer, or any combination of the two.

In various embodiments, an ECG device using signal processing to detect one or more subwaveforms within the P, Q, R, S, T, U, and J waveforms and/or within the intervals between the P, Q, R, S, T, U, and J waveforms is herein referred to as a saah ECG device. The voltage difference signals produced by a saah ECG device are referred to as saah ECG waveforms. The term "saah" is an acronym for some of the anatomically distinct portions of muscle tissue that produce subwaveforms. Specifically, saah stands for sinoatrial node (SAN), atria (right atrium (RA) and left atrium (LA)), atrioventricular node (AVN), and bundle of His (HIS). However, a saah ECG waveform is not limited to including subwaveforms representing the SAN, the atria, the AVN, and the HIS. A saah ECG waveform can include any subwaveform the P, Q, R, S, T, U, and J waveforms and/or within the intervals between the P, Q, R, S, T, U, and J waveforms.

Figure 9:
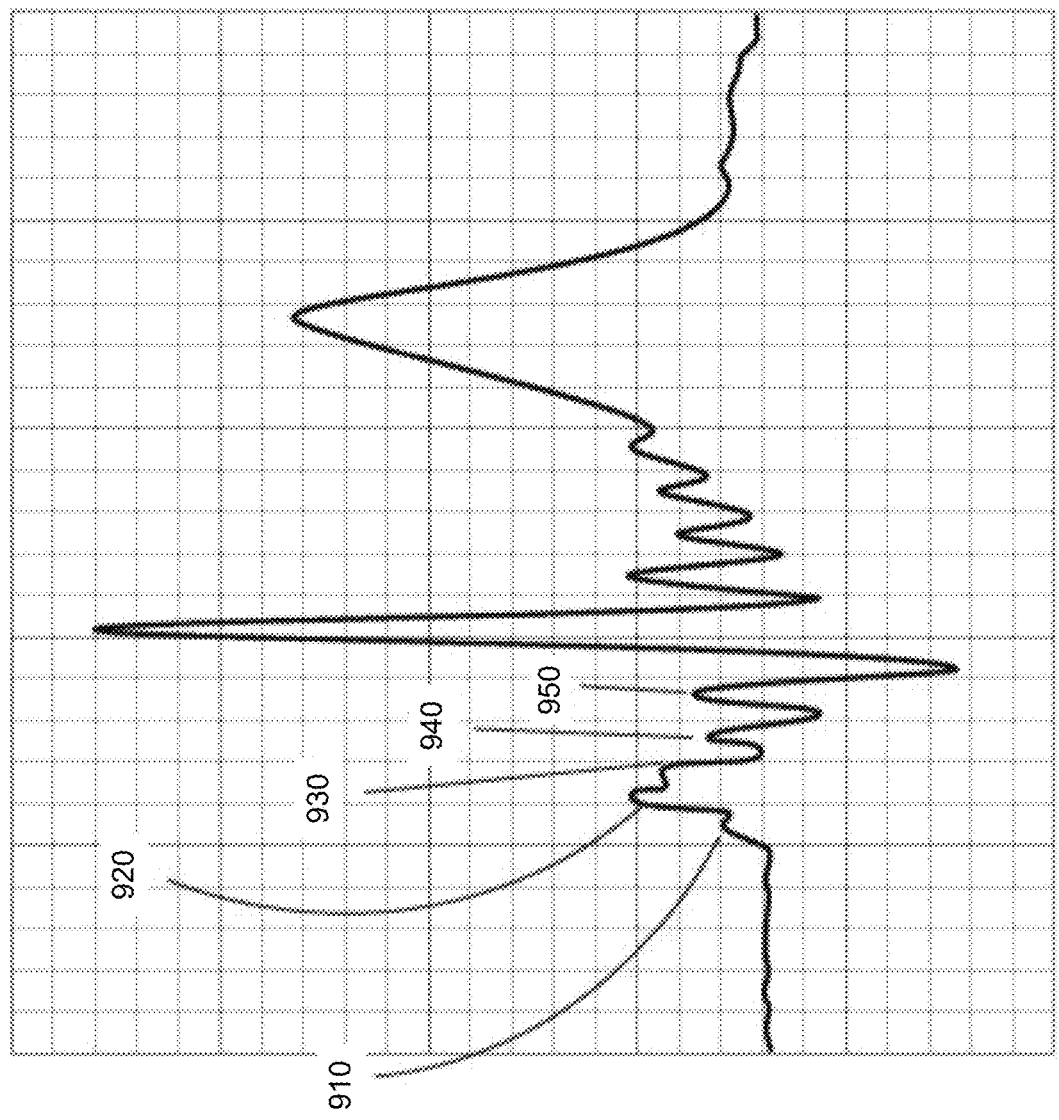
FIG. 9 is an exemplary plot of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments.

FIG. 9 is an exemplary plot 900 of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments. For example, five subwaveforms 910-950 of FIG. 9 are detected within the P waveform and the PR segment. The time period that includes the P waveform and the PR segment is also called the PR interval. Subwaveform 910 represents the depolarization of the SAN. Subwaveform 920 represents the depolarization of RA and LA. Subwaveform 930 represents the depolarization of the AVN. Subwaveform 940 represents the depolarization HIS. Finally, subwaveform 950 represents the depolarization of the bundle branches (BB).

In various embodiments, the subwaveforms of a saah ECG waveform are detected using signal processing. Electrodes 810 of the saah ECG of FIG. 8, for example, receive electrical impulses from anatomically distinct portions of muscle tissue or cells. The electrical impulses of anatomically distinct portions of muscle tissue of the heart have distinct frequencies. Through animal and human experimentation, the distinct frequency, frequency range, or frequency band of the anatomically distinct portions of muscle tissue of the heart are found. These distinct frequency bands of anatomically distinct portions of muscle tissue of the heart provide predetermined data or information for signal processing. In other words, the band pass frequency filtering of the signal processing is determined from the experimental data collected. A saah ECG device then employs one or more frequency band pass filters to detect the one or more subwaveforms.

Figure 10:
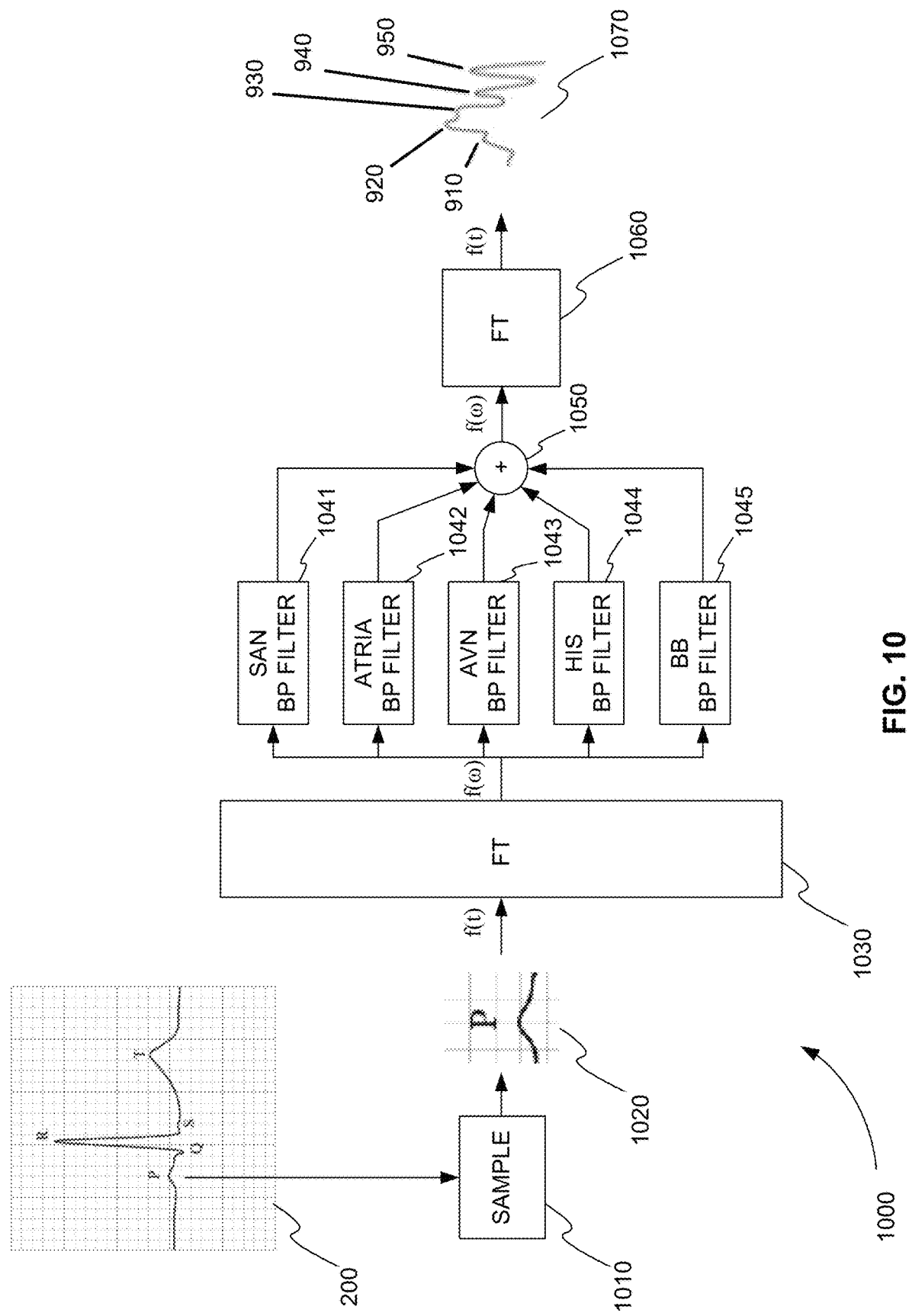
FIG. 10 is an exemplary block diagram showing a signal processing algorithm for detecting five subwaveforms within the PR interval of a conventional ECG waveform, in accordance with various embodiments.

FIG. 10 is an exemplary block diagram 1000 showing a signal processing algorithm for detecting five subwaveforms within the PR interval of a conventional ECG waveform, in accordance with various embodiments. Sampling block 1010 samples the electrical impulses in the PR interval time period of each heart. This is shown graphically in FIG. 1000 by separating PR interval 1020 from ECG waveform 200. The electrical impulses in the PR interval time period are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 10, block 1030 converts the PR interval time domain signal to a PR interval frequency domain signal. The time domain signal is converted into a frequency domain signal using a Fourier transform, for example.

As described above, through animal and/or human experimentation, the frequency bands associated with depolarization of the SAN, atria, AVN, HIS, and BB of the heart are determined. Based on these frequency bands, band pass filters are created. Blocks 1041-1045 represent the band pass filters created to filter the PR interval frequency domain signal for frequency bands of the SAN, atria, AVN, HIS, and BB of the heart, respectively.

In block 1050, the frequency domain subwaveforms detected from the band pass filtering the frequency bands of the SAN, atria, AVN, HIS, and BB of the heart are summed. In block 1060, the filtered and summed frequency domain signal of the PR interval is converted back to a time domain signal. The frequency domain signal is converted into a time domain signal using a Fourier transform, for example.

The PR interval filtered and summed time domain signal 1070 includes five time domain subwaveforms 910-950. Subwaveforms 910-950 represent depolarization of the SAN, atria, AVN, HIS, and BB of the heart, respectively. Time domain signal 1070 can be used to replace PR interval 1020 in ECG waveform 200, for example. As a result, a saah ECG waveform is produced.

FIG. 10 shows a signal processing algorithm for detecting five subwaveforms. However, similar steps can be applied to detect fewer than five waveforms or more than five waveforms. Also, the steps of FIG. 10 describe detecting subwaveforms within the PR interval. However, similar steps can be applied to detect subwaveforms within the P, Q, R, S, T, U, and J waveforms and/or within one or more of the intervals between the P, Q, R, S, T, U, and J waveforms. In addition, the steps of FIG. 10 describe converting time signals to the frequency domain and then back to the time domain. One of ordinary skill in the art can appreciate that band pass filters can be applied directly to the time domain signal to provide the same result.

Figure 11:
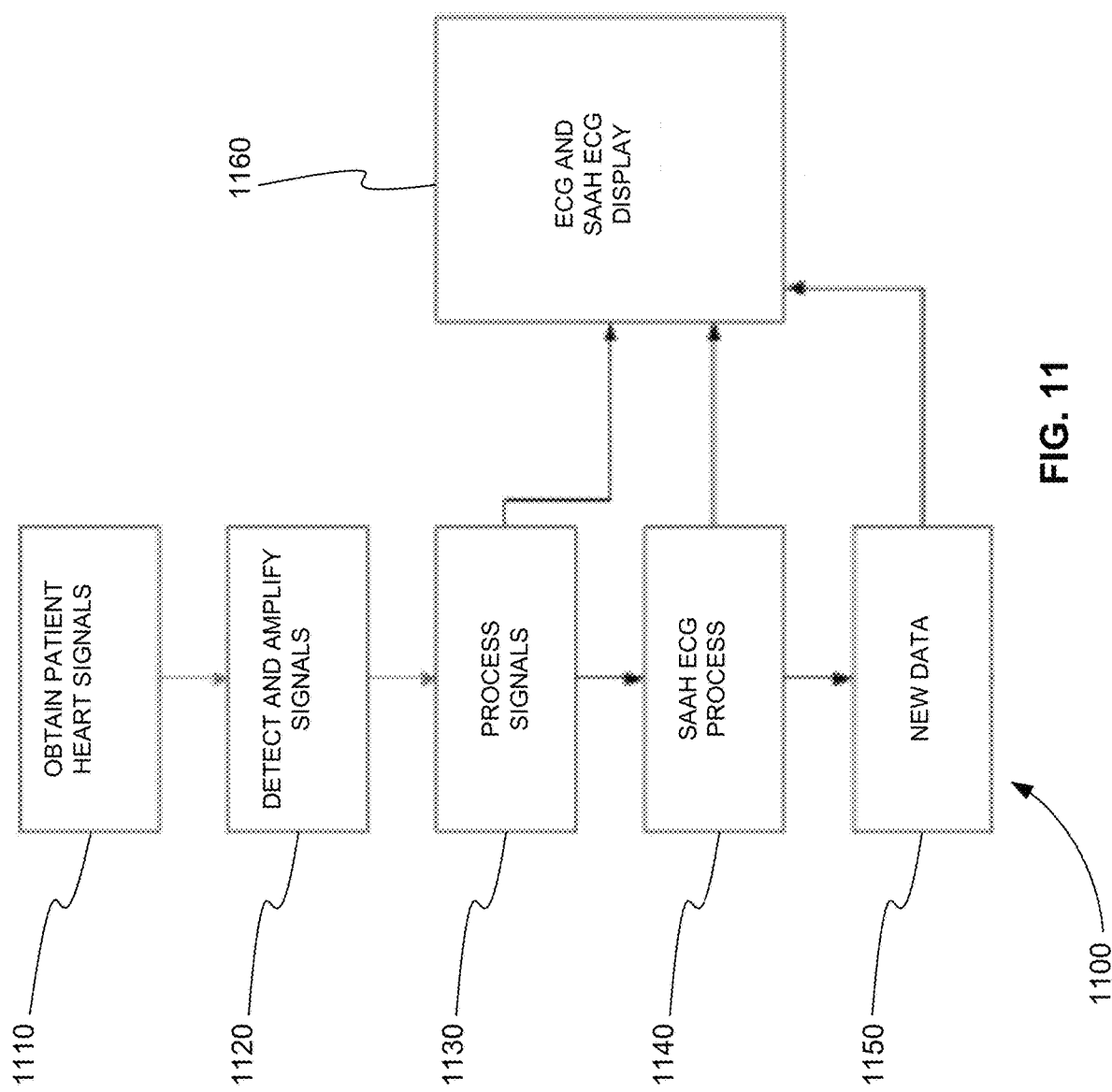
FIG. 11 is an exemplary block diagram of a saah ECG device that displays conventional ECG waveforms, saah ECG waveforms, and saah ECG data, in accordance with various embodiments.

FIG. 11 is an exemplary block diagram 1100 of a saah ECG device that displays conventional ECG waveforms, saah ECG waveforms, and saah ECG data, in accordance with various embodiments. In block 1110, patient heart signals are obtained. These heart signals can be obtained through noninvasive electrodes placed on the skin, such as electrodes 810 shown in FIG. 8. In various embodiments, heart signals may also be obtained using invasive electrodes placed directly on the heart. In block 1120, the heart signals are detected using a detector and amplified.

In block 1130, the detected and amplified heart signals are processed using a signal processor. The signal processor detects the conventional P, Q, R, S, T, U, and J waveforms and sends them to the display of block 1160. The signal processor also detects or calculates subwaveforms within the conventional P, Q, R, S, T, U, and J waveforms and/or within intervals between the conventional P, Q, R, S, T, U, and J waveforms. The signal processor sends the subwaveforms to block 1140 for further processing. The processor of block 1140 produces the saah ECG waveform that includes the subwaveforms and sends the saah ECG waveform to the display of block 1160. The processor of block 1140 calculates additional information or new data from the saah ECG waveform. This new data can include, but is not limited to, timing information about the subwaveforms, timing information about the intervals between the subwaveforms, and timing information about the subwaveforms and their relation to the conventional P, Q, R, S, T, U, and J waveforms. In block 1150, this new data is sent to the display of block 1160.

The display of block 1160 displays a continuous loop of the conventional ECG waveform, the saah ECG waveform, and the new data from the subwaveforms. The display of block 1160 can display this information on an electronic display or print it on paper. The display of block 1160 can also record this information. The display of block 1160 can record this information on any type of memory device.

Figure 12:
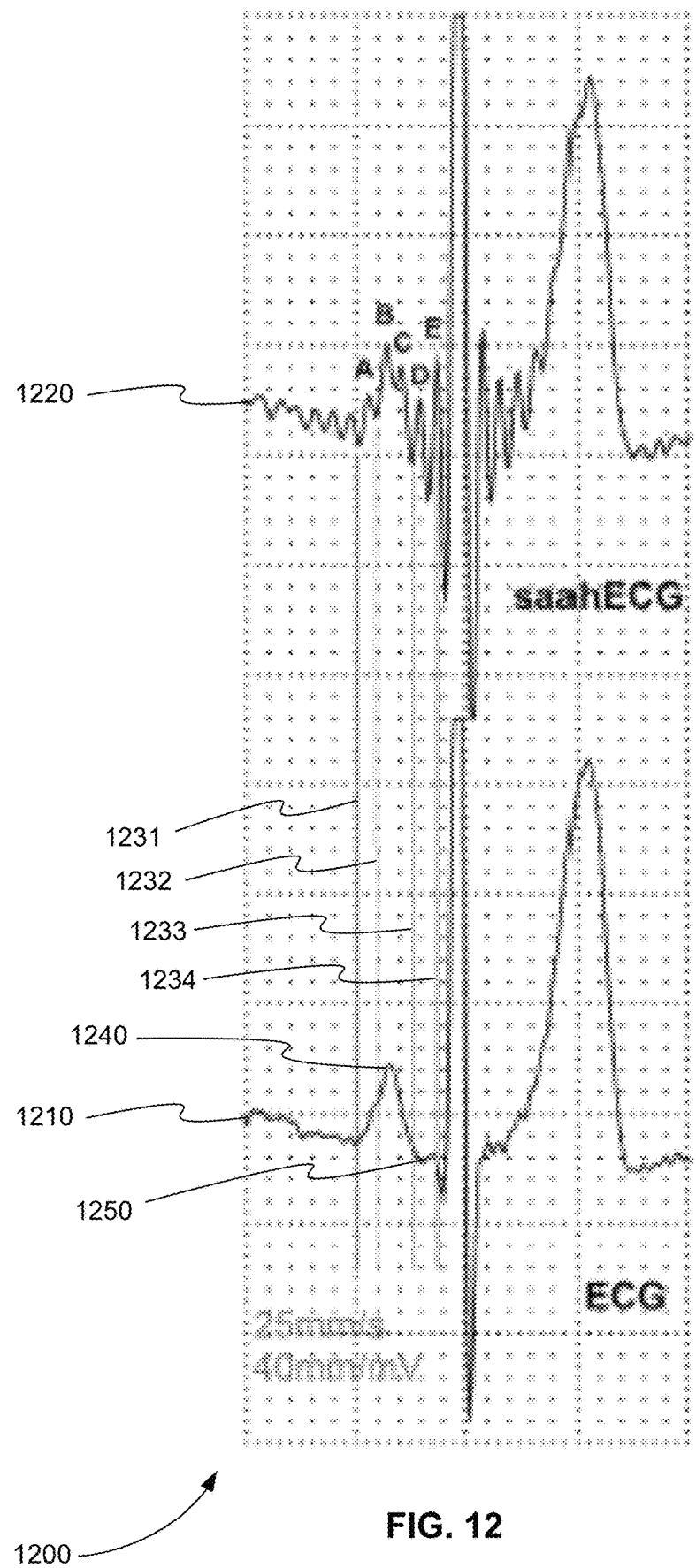
FIG. 12 is an exemplary plot of the information displayed by the saah ECG device of FIG. 10, in accordance with various embodiments.

FIG. 12 is an exemplary plot 1200 of the information displayed by the saah ECG device of FIG. 11, in accordance with various embodiments. Plot 1200 includes conventional ECG waveform 1210 and saah ECG waveform 1220. Saah ECG waveform 1220, for example, includes, among others, five subwaveforms A-E representing the depolarization of the SAN, the RA and LA, the AVN, the HIS, and the BB, respectively.

Plot 1200 also shows new data or timing information about the subwaveforms and their relation to the conventional P, Q, R, S, T, U, and J waveforms. For example, the time interval between line 1231 and line 1232 relates subwaveform A of saah ECG waveform 1220 to P waveform 1240 of conventional ECG waveform 1210. The time interval between line 1232 and line 1233 relates subwaveforms B and C of saah ECG waveform 1220 to P waveform 1240 conventional ECG waveform 1210. The time interval between line 1233 and line 1234 relates subwaveforms D and E of saah ECG waveform 1220 to PR segment 1250 conventional ECG waveform 1210.

Figure 13:
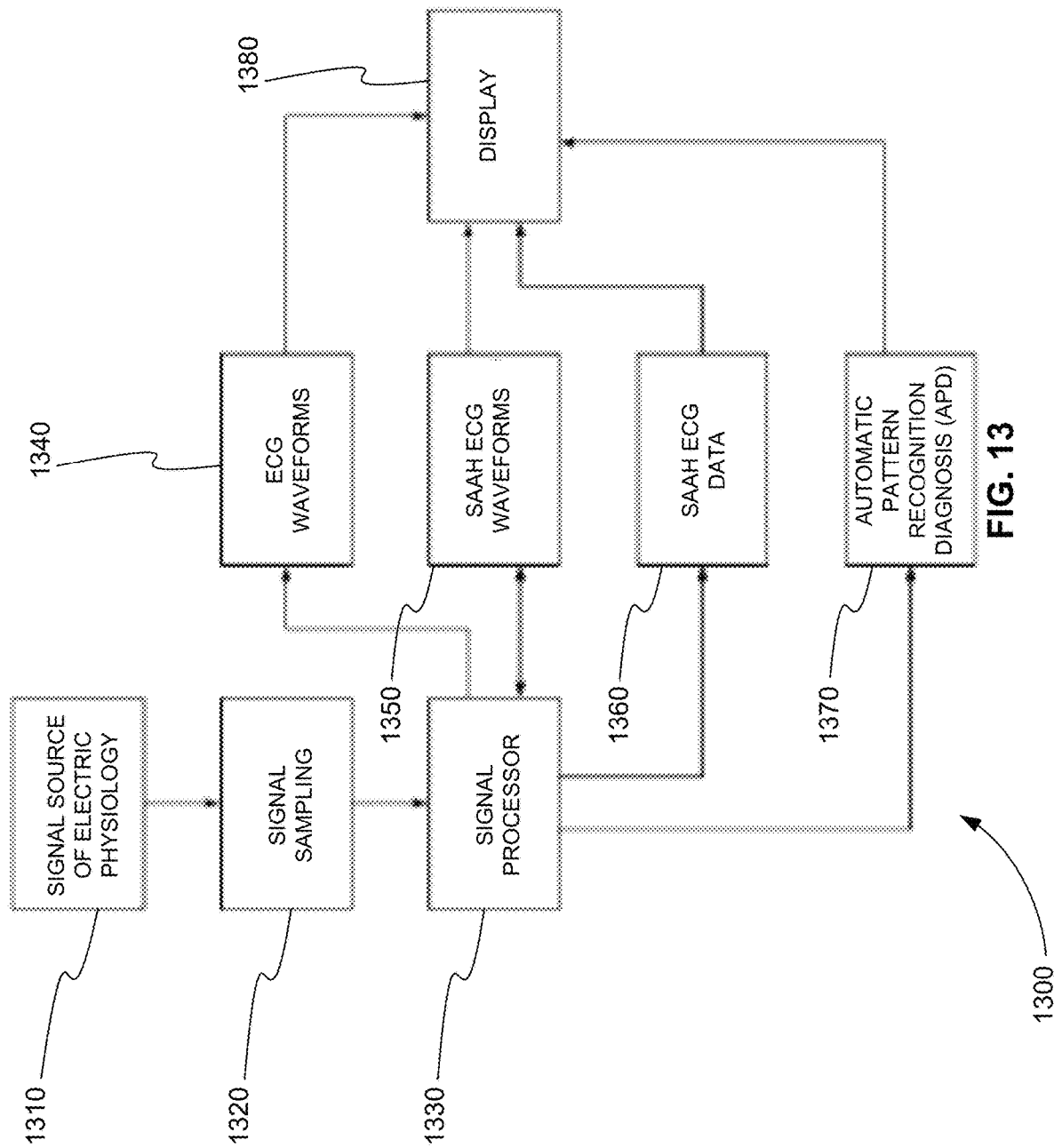
FIG. 13 is an exemplary block diagram of a saah ECG device that displays conventional ECG waveforms, saah ECG waveforms, saah ECG data, and saah ECG automatic pattern recognition diagnosis information, in accordance with various embodiments.

FIG. 13 is an exemplary block diagram 1300 of a saah ECG device that displays conventional ECG waveforms, saah ECG waveforms, saah ECG data, and saah ECG automatic pattern recognition diagnosis information, in accordance with various embodiments. In block 1310, patient heart signals are obtained. These heart signals can be obtained through noninvasive electrodes placed on the skin, such as electrodes 810 shown in FIG. 8. In various embodiments, heart signals may also be obtained using invasive electrodes placed directly on the heart. In block 1320, the heart signals are sampled or detected using a detector. The heart signals may also be amplified.

In block 1330, the sampled heart signals are processed using a signal processor. The signal processor produces four different types of information from the sampled heart signals. As shown in block 1340, the signal processor produces conventional ECG waveforms including the conventional P, Q, R, S, T, U, and J waveforms and sends them to display 1380. As shown in block 1350, the signal processor produces saah ECG waveforms. These saah ECG waveforms include subwaveforms of the conventional P, Q, R, S, T, U, and J waveforms and the intervals between them. Note that the arrow between blocks 1330 and 1350 show information following in both directions. This shows that information from the saah ECG waveforms is further analyzed by the signal processor.

As shown in block 1360, the signal processor further analyzes the saah ECG waveforms to produce saah ECG data. This saah ECG data is sent to display 1380. Additionally, as shown in block 1370, the signal processor further analyzes the saah to obtain endocardium and epicardium data. This data is compared to recorded normal and abnormal data. The signal processor then produces automatic pattern recognition diagnosis (APD) information, and this information is sent to display 1380. APD information is, for example, patterns and/or colors that allow a user to easily and quickly determine that normal or abnormal endocardium and/or epicardium data was found.

Systems and methods for detecting ECG subwaveforms are described in the '204 Patent, which is incorporated by reference in its entirety.

System for Detecting ECG Subwaveforms

In various embodiments, an electrocardiography (ECG) system for detecting one or more subwaveforms within the P, Q, R, S, T, U, and J waveforms or in an interval between the P, Q, R, S, T, U, and J waveforms is provided. Returning to FIG. 8, the ECG system includes two or more electrodes 810, a detector 820, a signal processor 830, and a display device 840.

Two or more electrodes 810 are placed near a beating heart and receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses. In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor 830 receives the ECG waveform from detector 820. Signal processor 830 detects or calculates one or more subwaveforms within P, Q, R, S, T, U, and J waveforms of the ECG waveform or in an interval between the P, Q, R, S, T, U, and J waveforms that represent the depolarization or repolarization of anatomically distinct portions of muscle tissue of the beating heart. Signal processor 830 produces a processed ECG waveform that includes the one or more subwaveforms for each heartbeat.

Signal processor 830 can be a separate device, can be software running on a device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general-purpose processor. A general purpose processor can include, but is not limited to, a microprocessor, a microcontroller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820, detects or calculates one or more subwaveforms within and/or in the interval between the P, Q, R, S, T, U, and J waveforms, and sends the detected and amplified different voltage signal and the one or more subwaveforms to display device 840.

Display device 840 receives the processed ECG waveform for each heartbeat and displays the processed ECG waveform for each heartbeat. The processed ECG waveform is called a saah ECG waveform, for example. As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record saah ECG waveforms, saah ECG data and conventional ECG waveforms and data. The memory device can be, but is not limited to, a volatile electronic memory, such as random access memory (RAM), a non-volatile electronic memory, such as electrically erasable programmable read-only memory (EEPROM or Flash memory), or a magnetic hard drive.

In various embodiments, the detected one or more subwaveforms include at least one subwaveform representing depolarization of the sinoatrial node (SAN), the atria (right atrium (RA) and left atrium (LA)), the atrioventricular node (AVN), the bundle of His (HIS), or the bundle branches (BB) of the beating heart.

In various embodiments, the display device 840 further displays the ECG waveform for comparison with the processed ECG waveform.

In various embodiments, signal processor 830 further calculates timing information about the one or more subwaveforms, timing information about the intervals between the one or more subwaveforms, and timing information about the one or more subwaveforms and their relation to the P, Q, R, S, T, U, and J waveforms of the ECG waveform for each heartbeat. Display device 840 further receives this timing information from signal processor 830. Display device 840 displays the timing information about the one or more subwaveforms, the timing information about the intervals between the one or more subwaveforms, and the timing information about the one or more subwaveforms and their relation to the P, Q, R, S, T, U, and J waveforms of the ECG waveform for each heartbeat.

In various embodiments, the ECG system further includes a memory device (not shown). The memory device receives the ECG waveform and the processed ECG waveform from the signal processor.

In various embodiments, the memory device further includes normally processed ECG waveform data. Normally processed ECG waveform data is stored on the memory device using signal processor 830 or a general-purpose processor (not shown). Signal processor 830 further compares the processed ECG waveform to the normally processed ECG waveform data and calculates a status condition based on the comparison. The status conditions are, for example, normal, suspicious, or abnormal.

In various embodiments, the ECG system includes a second display device (not shown) surrounding a rotating button (not shown). Signal processor 830 further sends a colored pattern to the second display device based on the status condition. The second display device provides automatic pattern recognition diagnosis (APD).

Method for Detecting ECG Subwaveforms

Figure 16:
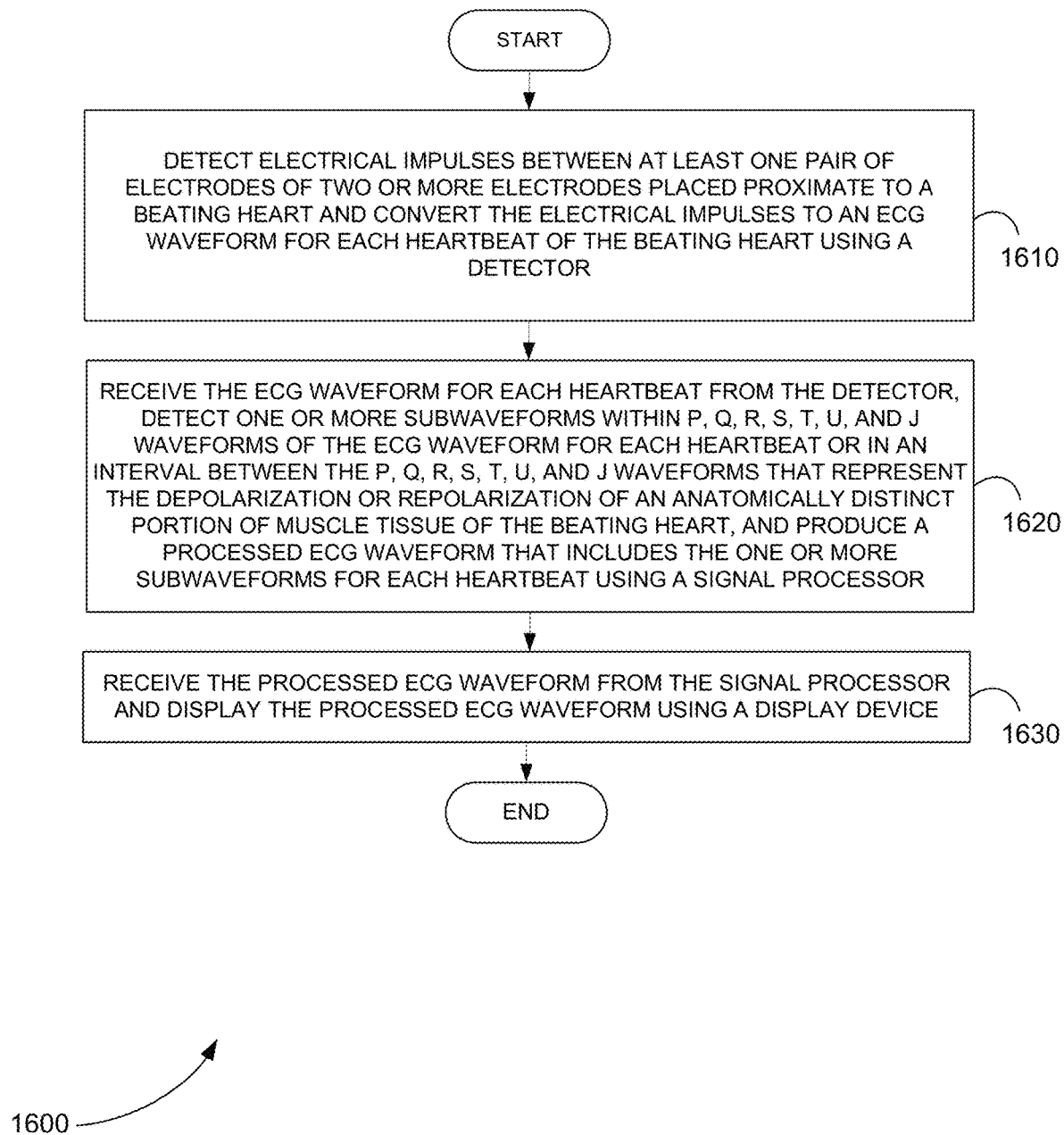
FIG. 16 is a flowchart showing a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 16 is a flowchart showing a method 1600 for detecting subwaveforms within the P, Q, R, S, T, U, and J waveforms of an ECG waveform of a heartbeat or in an interval between the P, Q, R, S, T, U, and J waveforms, in accordance with various embodiments.

In step 1610 of method 1600, electrical impulses are detected between at least one pair of electrodes of two or more electrodes placed proximate to a beating heart using a detector. The electrical impulses are converted to an ECG waveform for each heartbeat of the beating heart using the detector.

In step 1620, the ECG waveform for each heartbeat is received from the detector using a signal processor. One or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart are detected using the signal processor. A processed ECG waveform that includes the one or more subwaveforms for each heartbeat is produced using the signal processor.

In step 1630, the processed ECG waveform is received from the signal processor and the processed ECG waveform is displayed using a display device.

Computer Program Product for Detecting ECG Subwaveforms

In various embodiments, computer program products include a tangible computer-readable storage medium whose contents include a program with instructions being executed on a processor so as to perform a method for detecting subwaveforms within the P, Q, R, S, T, U, and J waveforms of an ECG waveform of a heartbeat or in an interval between the P, Q, R, S, T, U, and J waveforms. This method is performed by a system that includes one or more distinct software modules.

Figure 17:
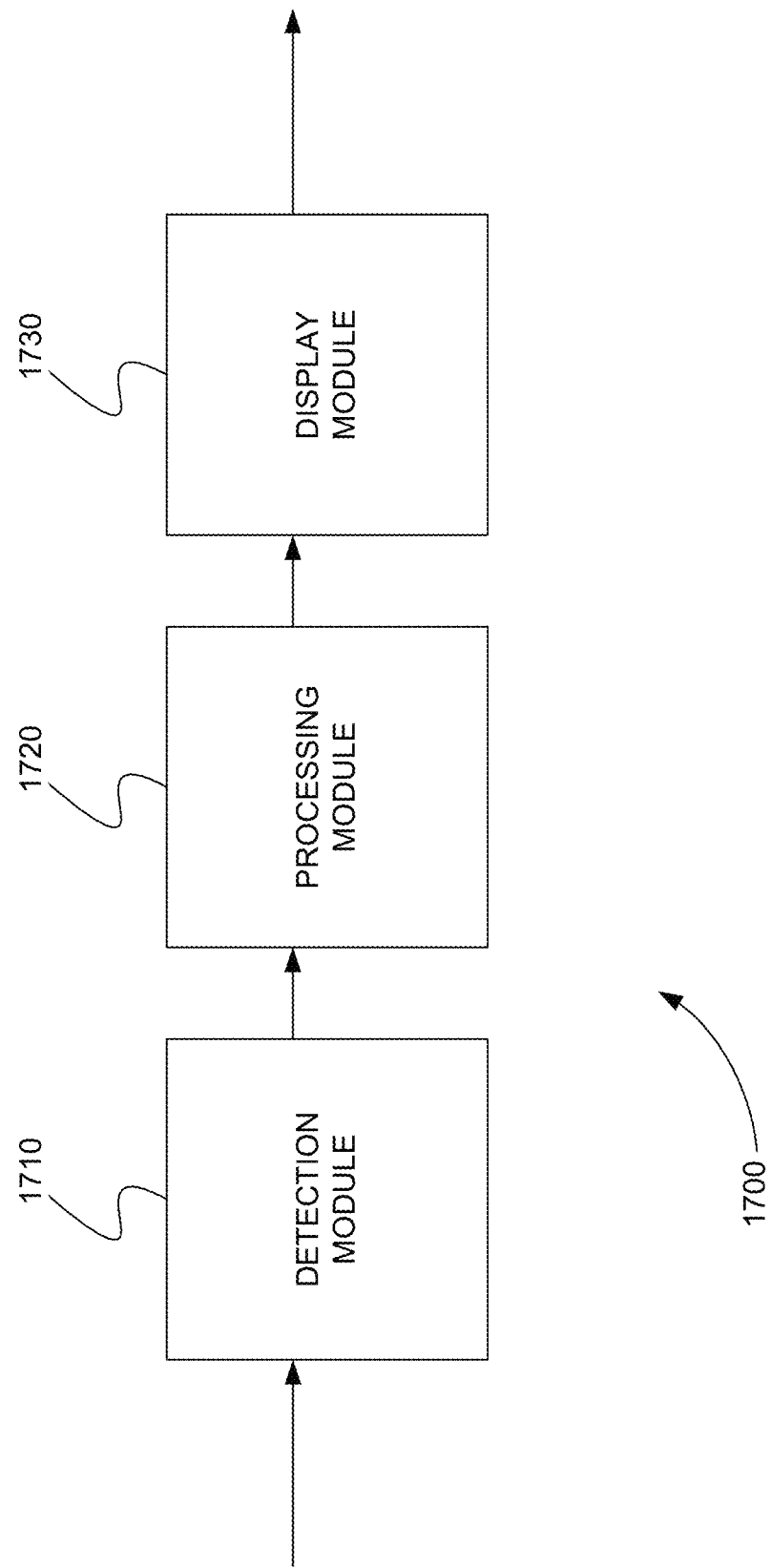
FIG. 17 is a schematic diagram of a system that includes one or more distinct software modules that perform a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 17 is a schematic diagram of a system 1700 that includes one or more distinct software modules that perform a method for detecting subwaveforms within the P, Q, R, S, T, U, and J waveforms of an ECG waveform of a heartbeat or in an interval between the P, Q, R, S, T, U, and J waveforms, in accordance with various embodiments. System 1700 includes detection module 1710, processing module 1720, and display module 1730.

Detection module 1710 detects electrical impulses between at least one pair of electrodes of two or more electrodes placed proximate to a beating heart. Detection module 1710 converts the electrical impulses to an ECG waveform for each heartbeat of the beating heart.

Processing module 1720 receives the ECG waveform for each heartbeat. Processing module 1720 detects one or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart. Processing module 1720 produces a processed ECG waveform that includes the one or more subwaveforms for each heartbeat.

Display module 1730 receives the processed ECG waveform. Display module 1730 displays the processed ECG waveform.

Automated ECG Analysis and Diagnosis

As described above, to date the accuracy rate of automated ECG analysis and diagnosis systems has been a problem in clinical applications. There are at least three technical reasons for this. 1. The conventional ECG waveform is morphological and generally no consistent mapping points can be found. 2. Conventional ECG measurements have not provided information specific different parts of the heart muscle. 3. Automated ECG waveform analysis has generally resulted in a high number of false positives for both normal and abnormal populations. However, ECG remains one of the most extensively used clinical tools, despite the lack of accurate systems for automated ECG analysis and diagnosis. As a result, there is a significant need for such systems. Recent advancements have addressed the conventional ECG waveform measurement problem. Specifically, the systems of the '204 Patent and the '930 Patent have allowed the different frequency domain signals from different parts of the heart muscle to be measured.

Additional systems, however, are needed to further address the technical problems of analyzing the shape and form of these frequency domain signals and distinguishing disease conditions from false positives in normal and abnormal populations.

Conventional ECG Waveform Analysis Problems

Analysis of conventional ECG waveforms for clinical diagnosis has been limited by a number of problems for more than a century. (1) It has been difficult to correctly confirm the start point of the P wave. The reason for this is that the start point of the P wave is on "a parallel equipotential line," which needs to be determined. This has traditionally been determined through guessing. If the starting point of each heartbeat cannot be correctly identified, then all subsequent parameter measurements will be wrong. The normal value for the conduction time from the SA node (the starting point of the P wave) to the atrium is only around 30 ms. As a result, a small mistake in the location of the starting point can make a big difference in the measurement of this conduction time.

Figure 14:
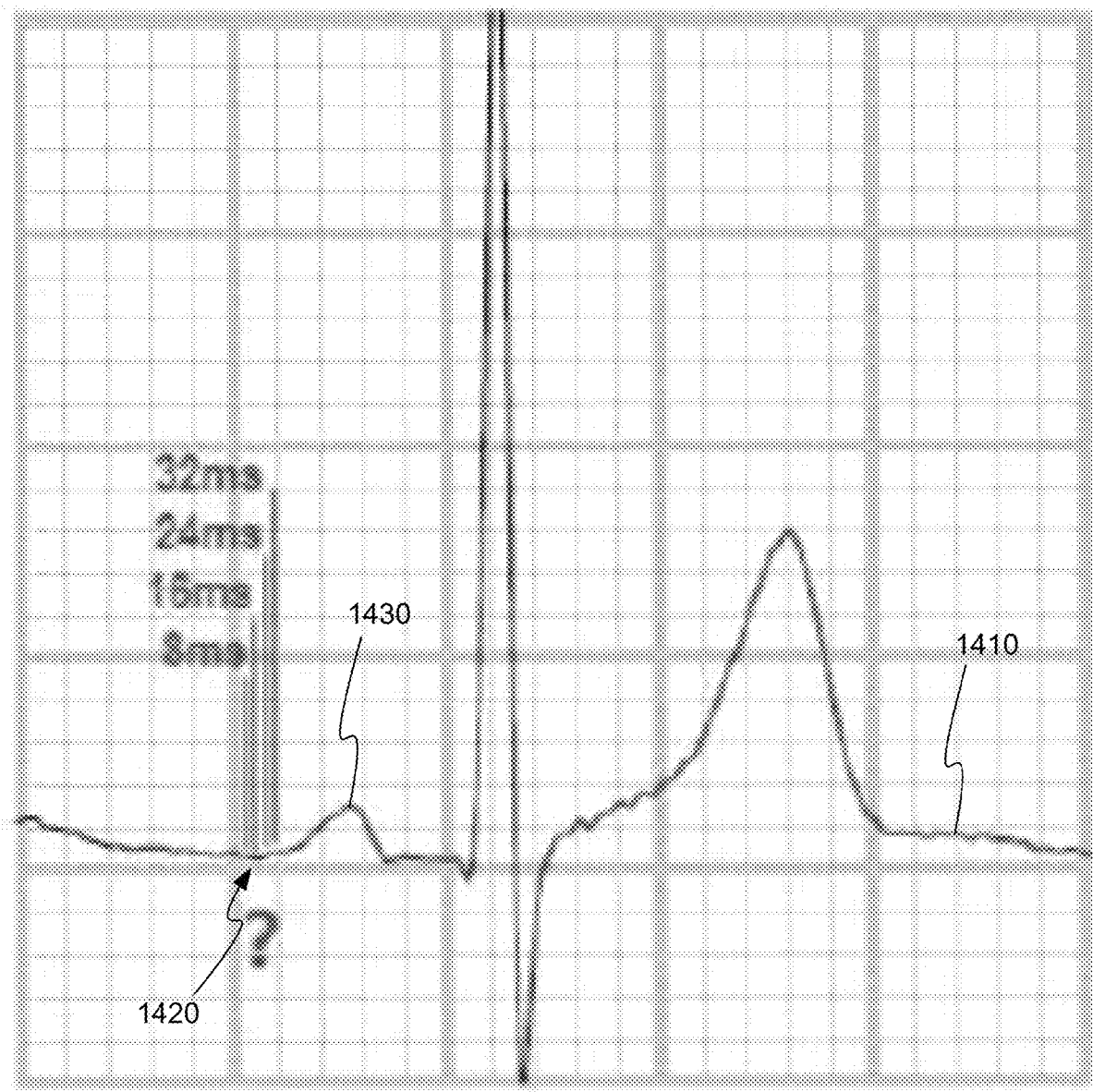
FIG. 14 is an exemplary plot of a conventional ECG waveform showing how a small error in the starting point of the P wave can cause a large error in all subsequent time measurements, in accordance with various embodiments.

FIG. 14 is an exemplary plot 1400 of a conventional ECG waveform showing how a small error in the starting point of the P wave can cause a large error in all subsequent time measurements, in accordance with various embodiments. The starting point of P wave 1430 of conventional ECG waveform 1410 is somewhere on parallel equipotential line 1420. Each square of the grid of plot 1400 represents a time of 40 milliseconds (ms). Parallel equipotential line 1420 spans about one square of the grid of plot 1400. As a result, picking four different closely spaced points along parallel equipotential line 1420 produces starting point times that vary among 8 ms, 16 ms, 24 ms, and 32 ms within the one square of the grid of plot 1400. In other words, small differences in the selection of the starting point of P wave 1430 can mean large differences in the timing values used for P wave 1430. It can also affect all of the other components of ECG waveform 1410. This is because the starting point of P wave 1430 is also the starting point of the entire ECG waveform 1410.

(2) At the PR interval, it has been difficult to identify the specific PA, AH, or HV intervals within PR interval. When the PR interval is abnormal, in particular, it can only be estimated and cannot be measured. Also, often the end of the PR interval cannot be confirmed, as there is no equipotential and the starting point of QRS wave appears to be an upward arc angle.

Figure 15:
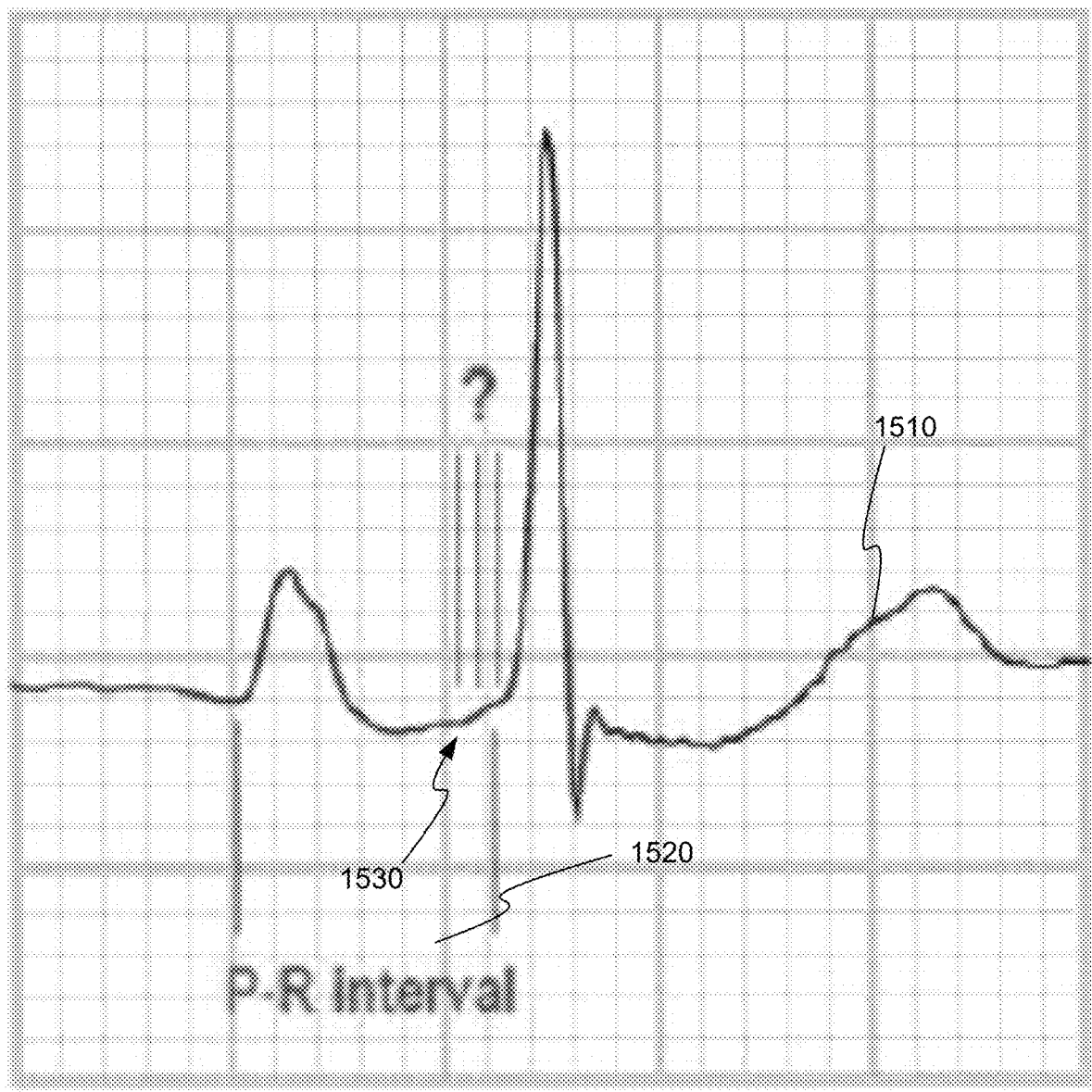
FIG. 15 is an exemplary plot of a conventional ECG waveform showing how the end of the PR interval cannot be confirmed due to an upward arc angle of the starting point of QRS wave, in accordance with various embodiments.

FIG. 15 is an exemplary plot 1500 of a conventional ECG waveform showing how the end of the PR interval cannot be confirmed due to an upward arc angle of the starting point of QRS wave, in accordance with various embodiments. The timing measurement of PR interval 1520 of conventional ECG waveform 1510 is a very important measurement since it the only measurement for the atrium. As described above, it is difficult to measure the starting point of the P wave, which is also the start of PR interval 1520. It turns out it is just as difficult if not more difficult to measure the ending point of PR interval 1520. This is due to changes to parallel equipotential line 1530 at the ending point of PR interval 1520 as shown in plot 1500. Parallel equipotential line 1530 is not parallel at all but rather is shaped like an upward arc angle. Therefore, it is very difficult to accurately map PR interval 1520. The standard value for PR interval 1520 is 120-200 ms, for example. In contrast, PR segment 220 of ideal conventional ECG waveform of FIG. 2 has a parallel equipotential line just before a downward arc angle to the QRS wave.

(3) It has been difficult to identify a difference between the ST segment of a normal person and the ST segment of an abnormal person. In other words, the ST segment appears to be exactly abnormal for normal people and exactly normal for abnormal people. Also, and the J point often disappears, making it impossible to determine. As a result, the standards for the ST segment often cannot be applied.

In summary, at an abnormal moment, signals of a conventional ECG waveform often shift positions, and the waveform is changed to a different shape, making it difficult or impossible to estimate. If a conventional ECG waveform is changed in such a way and human intelligence or experience is still relied on to diagnose, a large amount of accuracy is lost.

Automated ECG Analysis and Diagnosis Using AI

As described above, additional systems are needed to further address the technical problems of analyzing the shape and form of the frequency domain signals of a conventional ECG waveform and distinguishing disease conditions from false positives in normal and abnormal populations using the conventional ECG waveform.

In various embodiments, these technical problems are addressed by 1. applying artificial intelligence (AI) algorithms to characterize the shape and form of the frequency domain signals of a conventional ECG waveform; 2. comparing the characterized shape and form of the frequency domain signals to a database of characterized signals from normal and abnormal populations using human like AI algorithms and non-human like AI algorithms; and 3. annotating the conventional ECG waveform with diagnosis information based on the comparison.

Figure 18:
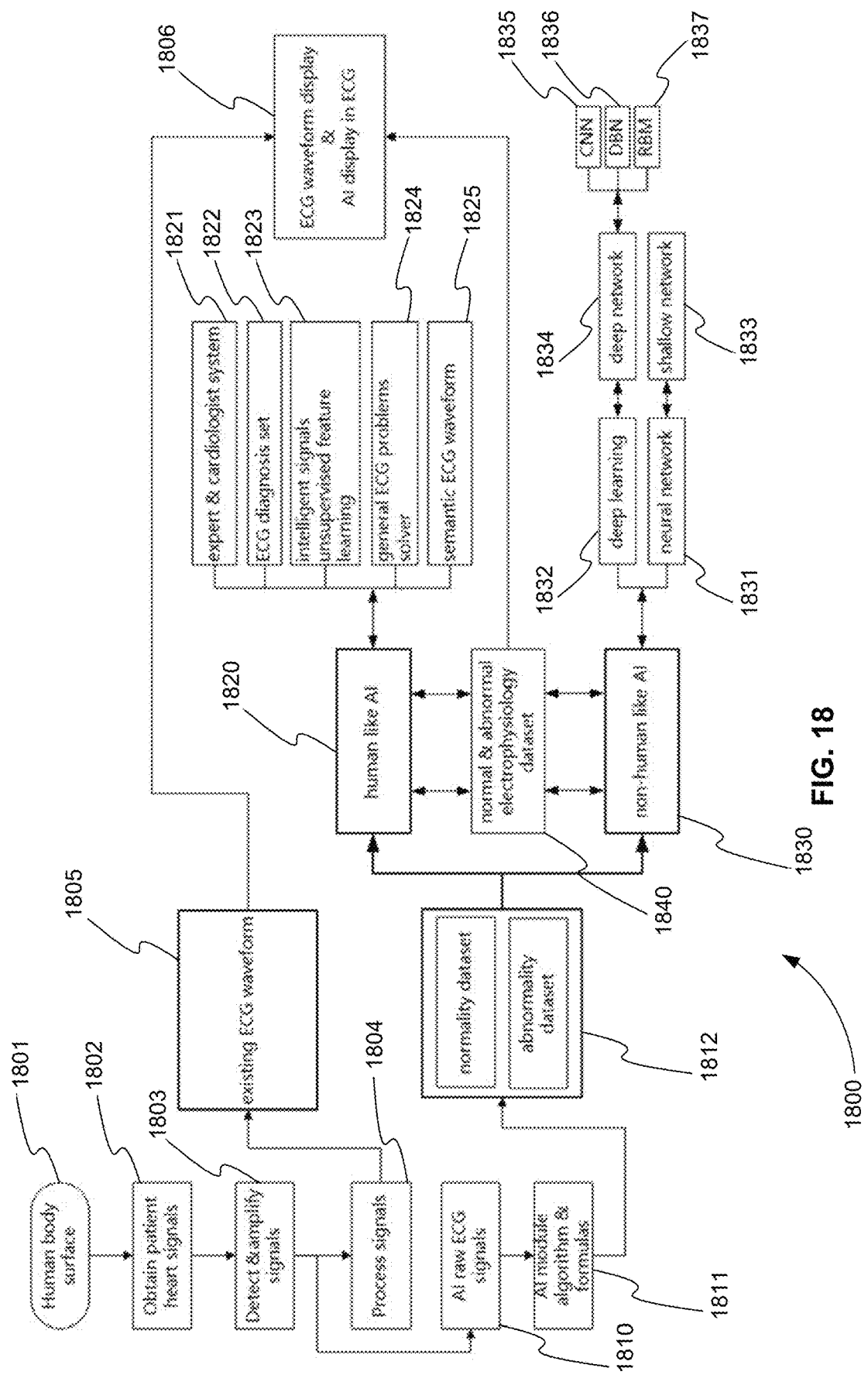
FIG. 18 is an exemplary block diagram of a system for automated ECG analysis and diagnosis using AI, in accordance with various embodiments.

FIG. 18 is an exemplary block diagram 1800 of a system for automated ECG analysis and diagnosis using AI, in accordance with various embodiments. In step 1801 of the system of FIG. 18, two or more electrodes are attached to the skin of a patient to obtain electrical signals from the heart muscle. In various alternative embodiments, the two or more electrodes may be attached directly and invasively to the heart muscle. The two or more electrodes are, for example, conventional ECG leads.

In step 1802, electrical heart signals are obtained from the two or more electrodes.

In step 1803, the electrical heart signals are detected and amplified.

In step 1804, the amplified signals are processed. For example, the signals from a number of different conventional ECG leads are combined.

In step 1805, the combined signals form a conventional ECG waveform.

In step 1806, the conventional ECG waveform is displayed or printed, for example.

In step 1810, the detected signals of step 1803 are obtained and processed to produce two or more frequency domain signals.

In step 1811, the two or more frequency domain signals are processed for characteristics of cardiac electrophysiological signals using one or more AI algorithms.

In step 1812, the cardiac electrophysiological characteristics of the two or more frequency domain signals are compared to databases of similar cardiac electrophysiological characteristics for normal and abnormal populations using the system of FIG. 18.

In step 1820, the cardiac electrophysiological characteristics of the two or more frequency domain signals are compared to the databases using human like AI algorithms. These human like AI algorithms can include, but are not limited to, an expert and cardiologist system 1821, an ECG diagnosis system 1822, an intelligent signals unsupervised feature learning system 1823, a general ECG problem solver 1824, and a semantic ECG waveform system 1825.

In step 1830, the cardiac electrophysiological characteristics of the two or more frequency domain signals are compared to the databases using non-human like AI algorithms. These human like AI algorithms can include, but are not limited to, a neural network algorithm 1831 and a deep learning algorithm 1832. The neural network algorithm 1831 can include a shallow network 1833. The deep learning algorithm 1832 can include a deep network 1834. This deep network 1834 can include, but is not limited to, a convolution all neural network (CNN) 1835, a deep belief net (DBN) 1836, or a restricted Boltzmann machine (RBM).

In step 1840, the results from steps 1820 and 1830 are combined to provide diagnosis information for the conventional ECG waveform.

In step 1806, this diagnosis information is displayed on the conventional ECG waveform.

The system of FIG. 18 provides a number of advantages over conventional automated analysis and diagnosis systems. First of all, it reduces medical and insurance expenses. As a result of the automated diagnosis information patients can avoid invasive and expensive examinations. Secondly, the quick and accurate diagnosis information allows prompt and accurate treatment. In other words, the shortened time for diagnosis allows treatment to occur without delay. Thirdly, the quick and accurate diagnosis helps train doctors more efficiently and can significantly reduce misdiagnosis rates. Fourthly, the quick and accurate diagnosis information can help in the research and development of new target drugs for cardiac treatments. Finally, the use of these AI algorithms in ECG makes these instruments intelligent systems.

In various embodiments, the diagnosis information presented in step 1806 can include, but is not limited to, diagnosis markers or more accurate timing information.

Analysis and Diagnosis System

The systems of the '204 Patent and the '930 Patent have used different signal processing methods to detect the harmonic signals and discontinuity points of a conventional ECG waveform. In various embodiments, artificial intelligence (AI) in conjunction with a database of normal and abnormal ECG data is used to detect the harmonic signals and discontinuity points of a conventional ECG waveform and to annotate cardiac electrophysiological signals in the ECG waveform as normal or abnormal.

Figure 19:
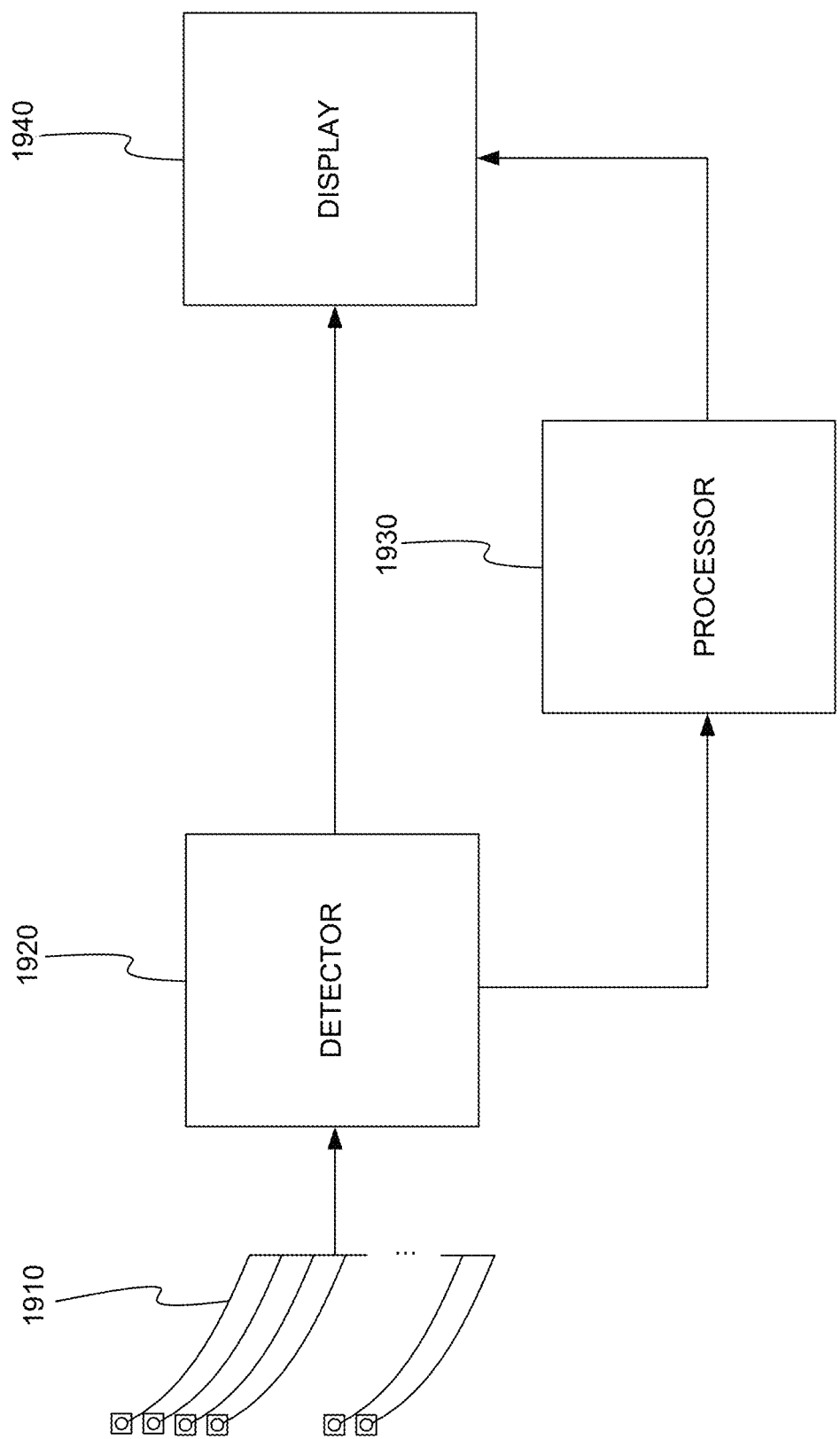
FIG. 19 is a block diagram of an ECG system for identifying and annotating cardiac electrophysiological signals in an ECG waveform as normal or abnormal during measurement of the ECG waveform, in accordance with various embodiments.

FIG. 19 is a block diagram 1900 of an ECG system for identifying and annotating cardiac electrophysiological signals in an ECG waveform as normal or abnormal during measurement of the ECG waveform, in accordance with various embodiments. Electrodes 1910 are attached to the skin of a patient in a noninvasive measurement, for example. In an alternative embodiment, electrodes 1910 are attached directly on the surface of a beating heart of a patient. Electrical signals produced by a beating heart are detected between pairs of electrodes 1910.

A voltage signal is detected between two electrodes 1910 by detector 1920. Detector 1920 also amplifies the voltage signal. Detector 1920 converts the electrical impulses to an ECG waveform for each heartbeat of the beating heart. Detector 1920 converts the voltage signal to a digital voltage signal using an analog to digital converter (A/D), for example. Detector 1920 provides the detected and amplified voltage signal from each pair of electrodes 1910 directly to display device 1940 to display the ECG waveform. The ECG waveform includes conventional P, Q, R, S, T, U, and J waveforms, for example. Detector 1920 also provides the detected and amplified voltage signal from each pair of electrodes 1910 directly to processor 1930.

Processor 1930 can be a separate electronic device that can include, but is not limited to, an application specific integrated circuit (ASIC), a field programmable gate array (FPGA), or a general-purpose processor or computer, such as the system of FIG. 1. Processor 1930 can be software implemented on another processor of the ECG device, such as a processor of display device 1940. Processor 1930 can also include a remote server computer.

Processor 1930 receives the ECG waveform for at least one heartbeat from detector 1920. Processor 1930 converts the ECG waveform to a frequency domain waveform. Processor 1930 separates the frequency domain waveform into two or more different frequency domain waveforms. Processor 1930 converts the two or more different frequency domain waveforms into a plurality of time domain cardiac electrophysiological subwaveforms and discontinuity points between these subwaveforms of the ECG waveform.

Processor 1930 compares the plurality of subwaveforms and discontinuity points to a database (not shown) of subwaveforms and discontinuity points for cardiac electrophysiological signals of ECG waveforms for a plurality of known and normal and abnormal patients. Processor 1930 identifies at least one subwaveform or one or more discontinuity points of the plurality of subwaveforms and discontinuity points as a normal or abnormal electrophysiological signal of the ECG waveform based on the comparison.

Display device 1940 is an electronic display device, a printer, or any combination of the two. Display device 1940 displays the ECG waveform for the at least one heartbeat of the beating heart. Display device 1940 also displays one or more markers at the location of the at least one subwaveform or the one or more discontinuity points on the ECG waveform and identifies the one or more markers as a normal or abnormal cardiac electrophysiological signal. For example, FIGS. 35 and 36 show how one or more markers are displayed on ECG waveforms to indicate normal or abnormal cardiac electrophysiological signals. The one or more markers can be identified as a normal or abnormal cardiac electrophysiological signal using symbols, colors, or text, for example.

In various embodiments, processor 1930 converts the ECG waveform to a frequency domain waveform, separates the frequency domain waveform into two or more different frequency domain waveforms, and converts the two or more different frequency domain waveforms into a plurality of time domain cardiac electrophysiological subwaveforms and discontinuity points using an artificial intelligence algorithm. The artificial intelligence algorithm includes a multivariable calculus algorithm, for example.

In various embodiments, processor 1930 compares the plurality of subwaveforms and discontinuity points to a database of subwaveforms and discontinuity points using a human like artificial intelligence algorithm.

In various embodiments, the human like artificial intelligence algorithm includes an expert and cardiologist system. This system evaluates the comparison based on morphological rules developed from cardiologists. In other words, the shape differences are compared using rules based on pattern recognition and doctors' experiences.

In various embodiments, the human like artificial intelligence algorithm includes an ECG diagnosis system. This system evaluates the comparison based on morphological patterns and their correlation to specific diseases.

In various embodiments, the human like artificial intelligence algorithm includes an intelligent signals unsupervised feature learning system. This system evaluates the comparison based on morphological patterns learned over time by the system.

In various embodiments, the human like artificial intelligence algorithm includes a general ECG problem solver. This system evaluates the comparison based on one or more known conditions or conflicting conditions including, but not limited to, heart failure (HF), atrium fibrillation (AF), atrial conductor block, premature atrial contraction (PAC), premature ventricular contraction (PVC), atrial tachycardia, and ventricular tachycardia.

In various embodiments, the human like artificial intelligence algorithm includes a semantic ECG waveform system. This system evaluates the comparison based on additional signal processing rather than pattern recognition.

In various embodiments, processor 1930 compares the plurality of subwaveforms and discontinuity points to a database of subwaveforms and discontinuity points using a non-human like artificial intelligence algorithm.

In various embodiments, the human like artificial intelligence algorithm includes a neural network. The neural network can be a shallow network, for example.

In various embodiments, the human like artificial intelligence algorithm includes a deep learning algorithm. The deep learning algorithm can include a deep network, for example. The deep network can include, but is not limited to, convolution all neural network (CNN), a deep belief net (DBN), or a restricted Boltzmann machine (RBM).

Vital Sign Monitoring

As described above, the ECG waveform is the most important parameter of Vital Sign Monitoring. Death is mainly caused by cardiac changes within the heart, even when there is no disease. The cardiac information changes from physiological to pathological. However, the current Vital Signs Monitor is only a warning device after the occurrence of critical events.

As a result, there is a need for Vital Sign Monitoring ECG systems and methods that provide automatic detection of possible disease and no longer simply act as an alarm device after the occurrence of critical events.

In various embodiments, a Vital Sign Monitoring ECG system correctly displays the signals that the traditional ECG cannot. It has key anatomical signals, including invasive parameters using noninvasive monitoring and fatal cardiac signals if/when abnormal events occur. It is able to scan, record, extract, analyze, and diagnose information lacking in traditional Vital Sign Monitoring.

In various embodiments, a Vital Sign Monitoring ECG system includes a ventricular monitoring module, capable of reading myocardial infarction without ST-T changes, acute coronary syndrome, acute myocardial ischemia, etc. This next-generation monitoring has three displays: a new ECG waveform, an artificial intelligence-based diagnostic color separation waveform, and quantitative data.

In various embodiments, a Vital Sign Monitoring ECG system does not solely rely on waveforms, contains automatic navigation, mapping of cardiac markers and diagnostic tools. This artificial intelligence (AI) system does not require a large database (because no two hearts are similar; each heartbeat is different and abnormal data varies even more). For example, the system can include a small database or rules derived from a database. The system does not take significant amounts of time. For example, 3-5 seconds of testing results in an automatic display.

In various embodiments, a Vital Sign Monitoring ECG system includes quantitative data for the new ECG waveform. Digital display is the most basic and critical requirement of a monitor. Traditional ECG's devices have many standardized data values, but they cannot be used because they cannot be measured precisely and are not automatically measured. Other monitoring devices use digitized data, such as Blood Pressure, SpO2, Heart Rate, Respiration Rate, Pulse Rate, and Temperature in order to achieve fast, accurate real-time information.

In various embodiments, a Vital Sign Monitoring ECG system includes a display that is a combination of cardiac electrophysiology and hemo-dynamics. The left and right ventricle are expressed in color; the display itself is expressed as a specified "form". This can be read easily, without training, and diagnosed within one second. This display reads faster than traditional data parameters, where after the monitor displays the data values, the doctor must then analyze and think about normal ranges.

In various embodiments, a Vital Sign Monitoring ECG system includes an anti-drift filter. In long-time monitoring, heart signal drift is the most common, major problem. Currently the best anti-drift filter is provided by the German company Philips. Their "linear phase filter and High-pass filter," however, removes the DC signal at the same time the left and right low-frequency signal is also removed. The resultant phase is seriously distorted because the low-frequency signal is removed at the same time; the lower-frequency signal is eliminated (extremely useful signal) and there are no mathematical changes.

The Vital Sign Monitoring ECG system includes an artificial intelligence automatic adjustable selection frequency segment. It understands which band is disturbed, and which band to remove. It also includes a variety of hybrid filters, including "linear and nonlinear phase" filters. It is very important that there is no phase distortion. The waveform is true, and the anti-drift effect is better. Drifts out of the display range are displayed as a straight line, signal overlapping and other serious drift signals are recoverable in this technology.

Figure 20:
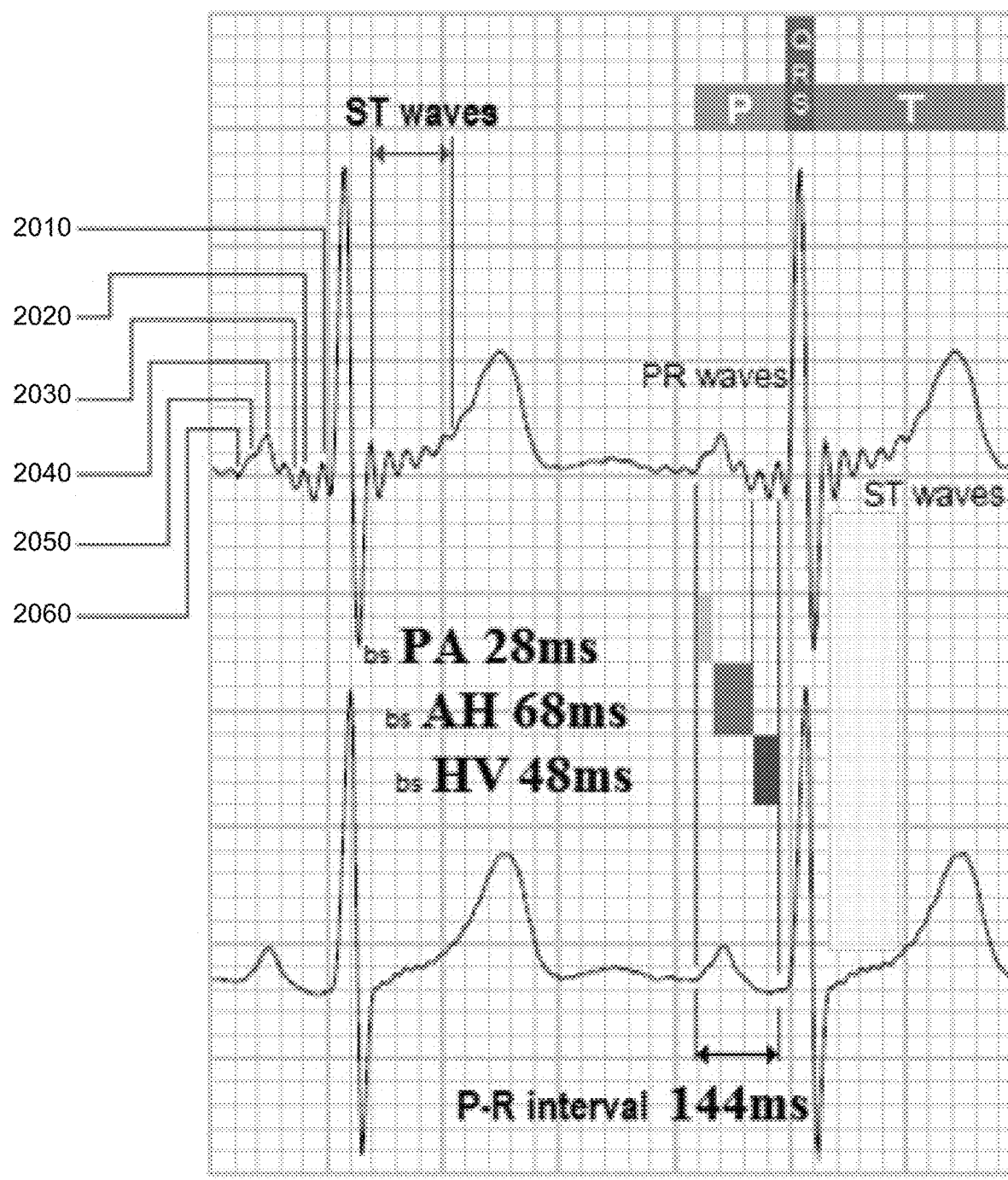
FIG. 20 is an exemplary diagram of a new ECG waveform and a corresponding traditional ECG waveform, in accordance with various embodiments.

FIG. 20 is an exemplary diagram 2000 of a new ECG waveform and a corresponding traditional ECG waveform, in accordance with various embodiments. The new or SAAH ECG waveform at the top of diagram 2000 shows additional subwaveforms and discontinuity points. For example, the new ECG waveform includes left and right bundle branches (BB) subwaveform 2010, bundle of HIS subwaveform 2020, point where AV node and bundle of HIS join 2030, AV node subwaveform 2040, point where AV node and Atrial area join 2050, and heart beat starting point 2060.

In contrast to the new ECG waveform, the traditional ECG waveform has no subwaveforms or wavelets in the P-R interval and the ST segment. The application of the new ECG waveform in Vital Sign Monitoring is more important because it can save time; every second is important in the ICU and enhance the real-world function of monitoring. The primary function of the Vital Sign Monitoring is to detect potential danger in advance, as well as Cardiac Risk Factors. While the current monitoring is only an alarm function. When the Heart Rate changes, ventricular fibrillation (VF) occurs, and/or ventricular tachycardia (VT) happens, it is too late for medical rescue.

Figure 21:
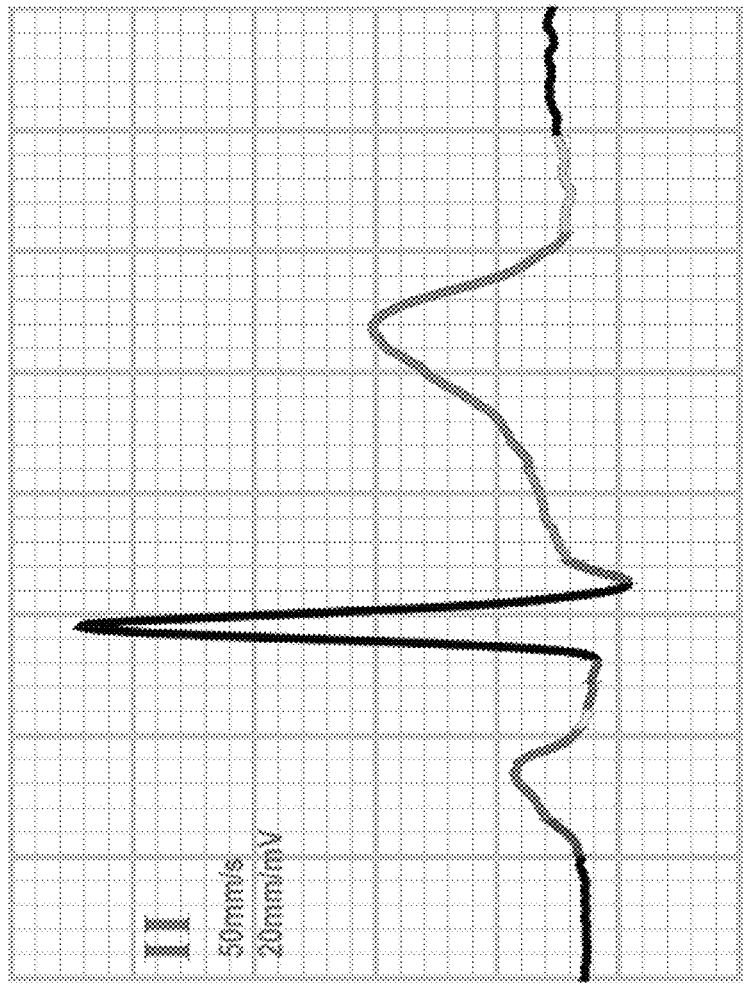
FIG. 21 is an exemplary diagram of an ECG diagnostic color separation waveform, in accordance with various embodiments.

FIG. 21 is an exemplary diagram 2100 of an ECG diagnostic color separation waveform, in accordance with various embodiments. The ECG diagnostic color separation waveform of diagram 2100 displays the anatomical parts of the heart in color within the P-R interval and ST-T interval, while the waveform itself is depicted as a traditional ECG waveform. Below the ECG diagnostic color separation waveform is a color key linking the colors to the anatomical parts of the heart. On the right are the parameter timing values with standard ranges and the test data. Doctors can search, review, and observe the normal time periods needed by patients in the monitor. When the data value exceeds the normal range, before a heart attack, before AMI, and before ACS, the number will automatically prompt an alarm. The doctor can choose different colors of the numbers. Current monitors only have a heart rate digital alarm.

Figure 22:
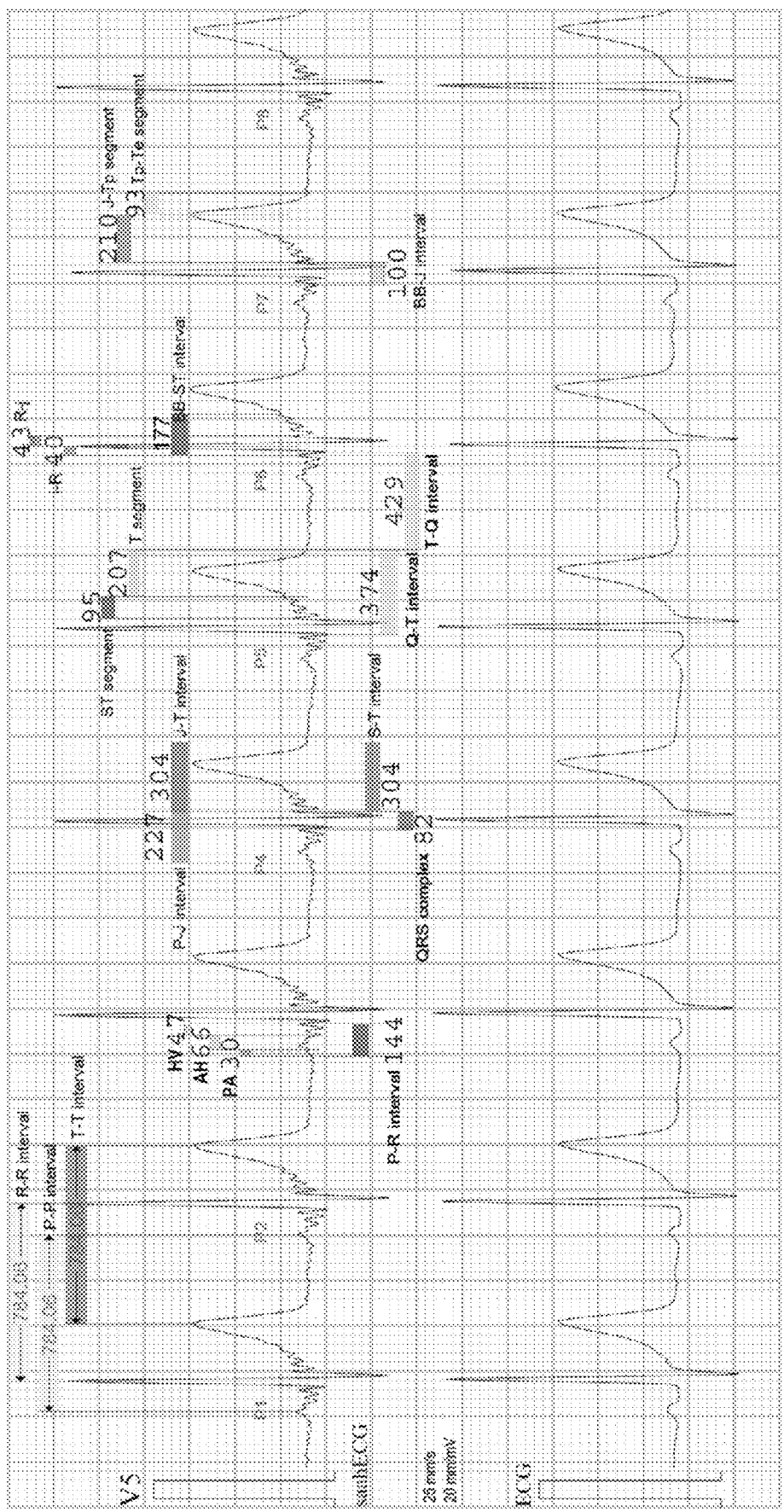
FIG. 22 is an exemplary diagram of a new ECG waveform and a corresponding traditional ECG waveform, showing some additional parameter timing values, in accordance with various embodiments.

FIG. 22 is an exemplary diagram 2200 of a new ECG waveform and a corresponding traditional ECG waveform, showing some additional parameter timing values, in accordance with various embodiments.

FIG. 23 is an exemplary table 2300 showing the timing parameter values of the ECG waveform in FIG. 22, including new timing parameter values, in accordance with various embodiments. Six timing parameter values are added including, BB-J interval 2310, BB-ST interval 2320, i-R segment 2330, R-j segment 2340, J-Tp 2350 (TP=[$1^{st}$ beat] T wave terminal point to [$2^{nd}$ beat] P wave initial point) segment, and T-T interval 2360. These parameters are applied in cases where the ECG waveform is finely changed and the judgment results are difficult to be made, such as wide QRS wave group, J-point vanishing, ST segment arc change, non-elevation or descent of ST segment, separation of atrium and ventricle, di-synchronization, degree of heart failure, and other image changes, which can be used to help analyze and judge the parameters.

BB-J Interval

For BB-J interval 2310, the timing is from Bundle branches to J-point. The most complex part is due to the anatomical features. The beam branch is divided into left bundle branch first and then right bundle branch. If block occurs, it will affect the shape and position of J-point. Once the starting point of the ST segment changes, the J-point will change with the delay of the bundle branch. The newly displayed J-point is not actually the original position, but is affected by the equipotential horizontal line. The J-point varies from point to point. Sometimes, it is convoluted in the QRS wave group and buried in the RS branch to form an elevation or a descent, resulting in the broadening of the QRS wave group. Traditional ECG is not shown. (This parameter cannot be measured by traditional ECG, because there are no measurement points in the BB region (there are no waves in the beam branch), and J-point displacement cannot be displayed). This parameter can be used to analyze whether it is simply left bundle branch block or right bundle branch block, or if it is left or right bundle branch block caused by J-point shift CAD. LCx vascular occlusion can easily cause left bundle branch block, and RCA vascular occlusion can easily cause right bundle branch block.

BB-ST Interval

For BB-ST interval 2320, the timing is from Bundle branches to ST segment. The key point of this part is the timing of the end of bundle branches and the connection segment of Purkinje's fibers. The traditional ECG cannot differentiate the end point of the ST segment. Data values of the initial interval from bundle branch to ventricular depolarization to ventricular repolarization can be analyzed. Increased analysis of left/right bundle branch block and CAD, heart failure, and other diseases, and analysis of primary and secondary lesions become available. In particular, when the ST segment is not elevated or descended, it is of great application value, because the H-P system (His-Purkinje's System) plays an extremely important role in the heart's power output, electrical excitation, and electrical conduction.

i-R Segment

For i-R segment 2330, the timing is for the path of the connection between the bundle branch and the initial end of the Purkinje's fibers to the maximum potential peak of ventricular depolarization. The anatomical location is located in the inner ventricular septum and the depolarizing position of the apex of the heart. Many diseases can cause signal variations, morphological changes, time lengthening, time shortening, time overlapping, or burial involving time segments, especially in the area of the P-R segment. These include patients with unrelenting Tachycardia, WPW, short PR syndrome, and so on. It is of great clinical significance in differential diagnosis and confirmation of normal and abnormal images. Traditional ECG cannot distinguish the precise position of the I-point and traditional ECG cannot accurately obtain i-R segment 2330 without the I-point position and its data value.

R-j Segment

This R-j segment, if the traditional ECG display is abnormal, is the most common and most difficult change to study. For R-j segment 2340, the timing is for the interval from the highest R wave peak of QRS to the terminal end of Purkinje's fibers. The anatomic location is the junction between the anterior wall and the apex of the free wall of the ventricle and the deep endocardium of Purkinje's terminal end. The R-j segment will be raised, lowered, lengthened, shortened, disappeared, inverted, etc. When a wide QRS wave group appears, J-point is embedded into RS. Meanwhile, the J-point position shown by the traditional ECG is the starting point of the equipotential line, rather than the real J-point. In traditional ECG, R peaks are easy to be identified, while J-point is not easy to be identified. R-S-J segments cannot be analyzed if they are widened. It is very important to confirm the data value of the R-j segment, which is imperative for distinguishing normal from abnormal. With traditional ECG is difficult to confirm the J-point, especially when the J-point is shifted, so it cannot be obtained without this parameter and data value.

J-Tp Segment

The difficulty of this parameter is in J-point positioning. In traditional ECG, the J-point is often a >120° arc angle and obtaining it with precision is extremely difficult. Tp is the peak of T wave, which is easy to locate. For J-Tp segment 2350, the timing is for the ST segment before ventricular repolarization—the highest peak of ventricular repolarization. The anatomical site is the site of cardiac systolic phase, phase II plus phase III. In this section of the new ECG, there are ST waves, which will show the loss of ST wavelets, increase, reach the peak of Tp, and the timing will change, shorten, extend, etc. When ST waves are disordered, it is not easy to calibrate. For traditional ECG, this segment it is not easy to measure because traditional ECG does not have ST waves and J-point data is not accurately acquired. This segment is of great significance when the ST segment is not elevated or descended.

T-T Interval

In the traditional ECG waveform, there are only R-R intervals and P-P intervals. The R-R interval is between first and second heartbeats (ventricular depolarization) and the P-P interval is between first and second heartbeats (atrial depolarization). T-T interval 2360 is measured between first and second heartbeats (ventricular repolarization). Since there is no atrial repolarization in the traditional ECG waveform, the T-T interval makes sense. These three intervals (P-P interval, R-R interval, T-T interval) need to be analyzed and judged at the same time. Alternatively, a P-P interval can be used to compare to a T-T interval, and a P-P interval is compared to an R-R interval to identify changes in the ventricular depolarization or repolarization. It is more convenient to apply quantitative data values to the Vital Sign Monitoring.

FIG. 24 is an exemplary diagram 2400 showing how heart signal drift is filtered, in accordance with various embodiments. Signals 2410 show heart signal drift. Signals 2420 show how heart signal drift is improved by applying an automatic identification anti-drift filter with automatic frequency selection. Even if data goes out of range, you get a straight line. If data goes out of the lead, you can basically recover and restore the original signal. As a result of long-time monitoring, the electrode produces polarization voltage and impedance increases. This occurs especially with a change of the indoor temperature and humidity in the clinical environment in winter. These temperature and humidity changes can easily produce electrical signal drift.

System for Displaying Intervals and Segments

In various embodiments, artificial intelligence (AI) in conjunction with a database of normal and abnormal ECG data is used to display and measure intervals and segments of an ECG waveform during measurement of the ECG waveform. This system is referred to as an aiECG system or a system for performing aiECG, for example.

Returning to FIG. 19, electrodes 1910 are attached to the skin of a patient in a noninvasive measurement, for example. In an alternative embodiment, electrodes 1910 are attached directly on the surface of a beating heart of a patient. Electrical signals produced by a beating heart are detected between pairs of electrodes 1910.

A voltage signal is detected between two electrodes 1910 by detector 1920. Detector 1920 also amplifies the voltage signal. Detector 1920 converts the electrical impulses to an ECG waveform for each heartbeat of the beating heart. Detector 1920 converts the voltage signal to a digital voltage signal using an analog to digital converter (A/D), for example. Detector 1920 provides the detected and amplified voltage signal from each pair of electrodes 1910 directly to display device 1940 to display the ECG waveform. The ECG waveform includes conventional P, Q, R, S, T, U, and J waveforms, for example. Detector 1920 also provides the detected and amplified voltage signal from each pair of electrodes 1910 directly to processor 1930.

Processor 1930 can be a separate electronic device that can include, but is not limited to, an application specific integrated circuit (ASIC), a field programmable gate array (FPGA), or a general-purpose processor or computer, such as the system of FIG. 1. Processor 1930 can be software implemented on another processor of the ECG device, such as a processor of display device 1940. Processor 1930 can also include a remote server computer.

Processor 1930 receives the ECG waveform for at least one heartbeat from detector 1920. Processor 1930 converts the ECG waveform to a frequency domain waveform. Processor 1930 separates the frequency domain waveform into two or more different frequency domain waveforms. Processor 1930 converts the two or more different frequency domain waveforms into a plurality of time domain cardiac electrophysiological subwaveforms and discontinuity points between these subwaveforms of the ECG waveform.

Processor 1930 compares the plurality of subwaveforms and discontinuity points to a database (not shown) of subwaveforms and discontinuity points for cardiac electrophysiological signals of ECG waveforms for a plurality of known and normal and abnormal patients or to a set of rules developed from the database. Processor 1930 identifies a bundle branches (BB) to J-Point (BB-J) interval from the comparison. The set of rules developed from the database can be, but are not limited to, AI rules or machine learning rules.

Display device 1940 is an electronic display device, a printer, or any combination of the two. Display device 1940 displays the ECG waveform with the BB-J interval annotated for the at least one heartbeat of the beating heart.

In various embodiments, processor 1930 further calculates a length of the BB-J interval in time and display device 1940 further displays the length of the BB-J interval in time for the at least one heartbeat of the beating heart.

In various embodiments, display device 1940 further displays a BB-J interval standard value range for the length of the BB-J interval. If the length of the BB-J interval is outside of the BB-J interval standard value range, display device 1940 displays the length of the BB-J interval in a different color and sounds an audible alarm.

In various embodiments, processor 1930 further identifies a BB to ST segment (B-ST) interval from the comparison and calculates a length of the BB-ST interval in time. Display device 1940 further displays the ECG waveform with the BB-ST interval annotated and displays the length of the BB-ST interval in time for the at least one heartbeat of the beating heart.

In various embodiments, display device 1940 further displays a BB-ST interval standard value range for the length of the BB-ST interval. If the length of the BB-ST interval is outside of the BB-ST interval standard value range, display device 1940 displays the length of the BB-ST interval in a different color and sounds an audible alarm.

In various embodiments, processor 1930 further identifies an i-R segment between an initial end of the Purkinje's fibers (I-point) to a maximum peak of ventricular depolarization (R) from the comparison and calculates a length of the i-R segment in time. Display device 1940 further displays the ECG waveform with the i-R segment annotated and displays the length of the i-R segment in time for the at least one heartbeat of the beating heart.

In various embodiments, display device 1940 further displays an i-R segment standard value range for the length of the i-R segment. If the length of the i-R segment is outside of the i-R segment standard value range, display device 1940 displays the length of the i-R segment in a different color and sounds an audible alarm.

In various embodiments, processor 1930 further identifies an R-j segment between a maximum peak of ventricular depolarization (R) and a terminal end of the Purkinje's fibers (J-Point) from the comparison and calculates a length of the R-j segment in time. Display device 1940 further displays the ECG waveform with the R-j segment annotated and displays the length of the R-j segment in time for the at least one heartbeat of the beating heart.

In various embodiments, display device 1940 further displays an R-j segment standard value range for the length of the R-j segment. If the length of the R-j segment is outside of the R-j segment standard value range, display device 1940 displays the length of the R-j segment in a different color and sounds an audible alarm.

In various embodiments, processor 1930 further identifies a J-Tp segment between a terminal end of the Purkinje's fibers (J-point) and a maximum peak of ventricular repolarization (Tp) from the comparison and calculates a length of the J-Tp segment in time. Display device 1940 further displays the ECG waveform with the J-Tp segment annotated and displays the length of the J-Tp segment in time for the at least one heartbeat of the beating heart.

In various embodiments, display device 1940 further displays a J-Tp segment standard value range for the length of the J-Tp segment. If the length of the J-Tp segment is outside of the J-Tp segment standard value range, display device 1940 displays the length of the J-Tp segment in a different color and sounds an audible alarm.

In various embodiments, processor 1930 further identifies a T-T interval between a maximum peak of ventricular repolarization (Tp) of a first heartbeat and a maximum peak of ventricular repolarization (Tp) of a second heartbeat from the comparison and calculates a length of the T-T interval in time. Display device 1940 further displays the ECG waveform with the T-T interval annotated and displays the length of the T-T interval in time for the at least one heartbeat of the beating heart.

In various embodiments, display device 1940 further displays a T-T interval standard value range for the length of the T-T interval. If the length of the T-T interval is outside of the T-T interval standard value range, display device 1940 displays the length of the T-T interval in a different color and sounds an audible alarm.

Method for Displaying Intervals and Segments

Figure 25:
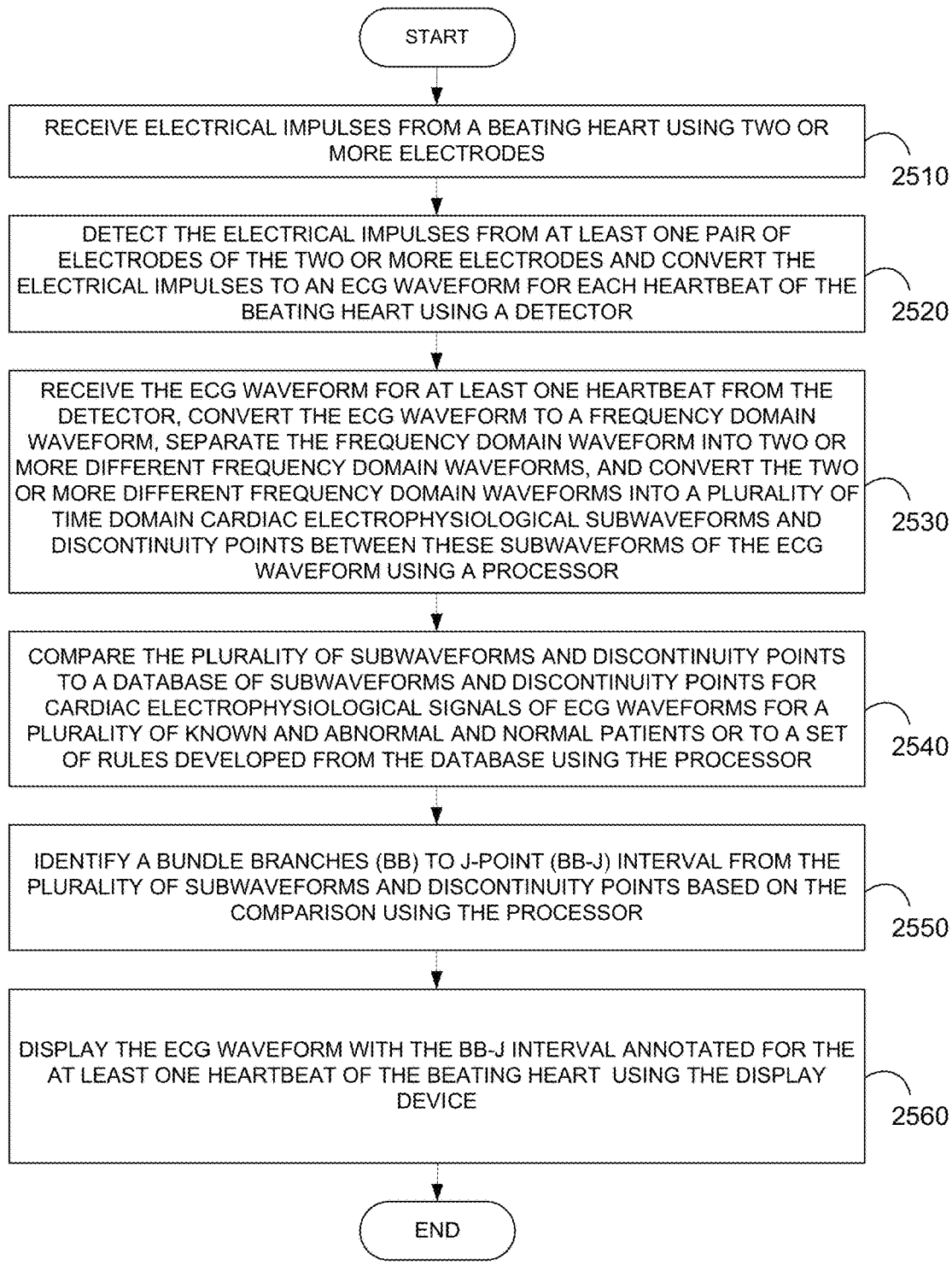
FIG. 25 is a flowchart showing a method for displaying and measuring intervals and segments of an ECG waveform during measurement of the ECG waveform, in accordance with various embodiments.

FIG. 25 is a flowchart showing a method 2500 for displaying and measuring intervals and segments of an ECG waveform during measurement of the ECG waveform, in accordance with various embodiments.

In step 2510 of method 2500, electrical impulses are received from a beating heart using two or more electrodes.

In step 2520, the electrical impulses are detected from at least one pair of electrodes of the two or more electrodes and converted to an ECG waveform for each heartbeat of the beating heart using a detector.

In step 2530, the ECG waveform for at least one heartbeat is received from the detector, the ECG waveform is converted to a frequency domain waveform, the frequency domain waveform is separated into two or more different frequency domain waveforms, and the two or more different frequency domain waveforms are converted into a plurality of time domain cardiac electrophysiological subwaveforms and discontinuity points between these subwaveforms of the ECG waveform using a processor.

In step 2540, the plurality of subwaveforms and discontinuity points are compared to a database of subwaveforms and discontinuity points for cardiac electrophysiological signals of ECG waveforms for a plurality of known and normal and abnormal patients or to a set of rules developed from the database using the processor.

In step 2550, a bundle branches (BB) to J-Point (BB-J) interval is identified from the plurality of subwaveforms and discontinuity points based on the comparison using the processor.

In step 2560, the ECG waveform with the BB-J interval annotated is displayed for the at least one heartbeat of the beating heart using the display device.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A noninvasive electrocardiography (ECG) system for displaying and measuring intervals and segments of an ECG waveform during measurement of the ECG waveform, comprising:

two or more electrodes adapted to be located near a beating heart of a patient and attached to the skin of the patient that receive electrical impulses from the beating heart;

a detector that detects the electrical impulses from at least one pair of electrodes of the two or more electrodes and converts the electrical impulses to an ECG waveform for each heartbeat of the beating heart;

a processor that receives the ECG waveform for at least one heartbeat from the detector, converts the ECG waveform to a frequency domain waveform, separates the frequency domain waveform into two or more different frequency domain waveforms, and converts the two or more different frequency domain waveforms into a plurality of time domain cardiac electrophysiological subwaveforms and discontinuity points between these subwaveforms of the ECG waveform, compares the plurality of subwaveforms and discontinuity points to a database of subwaveforms and discontinuity points for cardiac electrophysiological signals of ECG waveforms for a plurality of known and normal and abnormal patients or to a set of rules developed from the database, and identifies a bundle branches (BB) to J-Point (BB-J) interval from the comparison, calculates a length of the BB-J interval in time; and a display device that displays the ECG waveform with the BB-J interval annotated and displays the length of the BB-J interval in time for the at least one heartbeat of the beating heart.

2. The ECG system of claim 1, wherein the display device further displays a BB-J interval standard value range for the length of the BB-J interval and, if the length of the BB-J interval is outside of the BB-J interval standard value range, displays the length of the BB-J interval in a different color and sounds an audible alarm.

3. The ECG system of claim 1, wherein the processor further identifies a BB to ST segment (B-ST) interval from the comparison and calculates a length of the BB-ST interval in time and wherein the display device further displays the ECG waveform with the BB-ST interval annotated and displays the length of the BB-ST interval in time for the at least one heartbeat of the beating heart.

4. The ECG system of claim 3, wherein the display device further displays a BB-ST interval standard value range for the length of the BB-ST interval and, if the length of the BB-ST interval is outside of the BB-ST interval standard value range, displays the length of the BB-ST interval in a different color and sounds an audible alarm.

5. The ECG system of claim 1, wherein the processor further identifies an i-R segment between an initial end of the Purkinje's fibers (I-point) to a maximum peak of ventricular depolarization (R) from the comparison and calculates a length of the i-R segment in time and wherein the display device further displays the ECG waveform with the i-R segment annotated and displays the length of the i-R segment in time for the at least one heartbeat of the beating heart.

6. The ECG system of claim 5, wherein the display device further displays an i-R segment standard value range for the length of the i-R segment and, if the length of the i-R segment is outside of the i-R segment standard value range, displays the length of the i-R segment in a different color and sounds an audible alarm.

7. The ECG system of claim 1, wherein the processor further identifies an R-j segment between a maximum peak of ventricular depolarization (R) and a terminal end of the Purkinje's fibers (J-Point) from the comparison and calculates a length of the R-j segment in time and wherein the display device further displays the ECG waveform with the R-j segment annotated and displays the length of the R-j segment in time for the at least one heartbeat of the beating heart.

8. The ECG system of claim 7, wherein the display device further displays an R-j segment standard value range for the length of the R-j segment and, if the length of the R-j segment is outside of the R-j segment standard value range, displays the length of the R-j segment in a different color and sounds an audible alarm.

9. The ECG system of claim 1, wherein the processor further identifies a J-Tp segment between a terminal end of the Purkinje's fibers (J-point) and a maximum peak of ventricular repolarization (Tp) from the comparison and calculates a length of the J-Tp segment in time and wherein the display device further displays the ECG waveform with the J-Tp segment annotated and displays the length of the J-Tp segment in time for the at least one heartbeat of the beating heart.

10. The ECG system of claim 9, wherein the display device further displays a J-Tp segment standard value range for the length of the J-Tp segment and, if the length of the J-Tp segment is outside of the J-Tp segment standard value range, displays the length of the J-Tp segment in a different color and sounds an audible alarm.

11. The ECG system of claim 1, wherein the processor further identifies a T-T interval between a maximum peak of ventricular repolarization (Tp) of a first heartbeat and a maximum peak of ventricular repolarization (Tp) of a second heartbeat from the comparison and calculates a length of the T-T interval in time and wherein the display device further displays the ECG waveform with the T-T interval annotated and displays the length of the T-T interval in time for the at least one heartbeat of the beating heart.

12. The ECG system of claim 11, wherein the display device further displays a T-T interval standard value range for the length of the T-T interval and, if the length of the T-T interval is outside of the T-T interval standard value range, displays the length of the T-T interval in a different color and sounds an audible alarm.

13. A method for displaying and measuring intervals and segments of an electrocardiography (ECG) waveform during measurement of the ECG waveform, comprising:
receiving electrical impulses from a beating heart using two or more electrodes;
detecting the electrical impulses from at least one pair of electrodes of the two or more electrodes and converting the electrical impulses to an ECG waveform for each heartbeat of the beating heart using a detector;
receiving the ECG waveform for at least one heartbeat from the detector, converting the ECG waveform to a frequency domain waveform, separating the frequency domain waveform into two or more different frequency domain waveforms, and converting the two or more different frequency domain waveforms into a plurality of time domain cardiac electrophysiological subwaveforms and discontinuity points between these subwaveforms of the ECG waveform using a processor;
comparing the plurality of subwaveforms and discontinuity points to a database of subwaveforms and discontinuity points for cardiac electrophysiological signals of ECG waveforms for a plurality of known and normal and abnormal patients or to a set of rules developed from the database using the processor;
identifying a bundle branches (BB) to J-Point (BB-J) interval from the plurality of subwaveforms and discontinuity points based on the comparison using the processor; and
displaying the ECG waveform with the BB-J interval annotated for the at least one heartbeat of the beating heart using the display device.

14. The method of claim 13, further comprising
displaying a BB-J interval standard value range for the length of the BB-J interval using the display device and
if the length of the BB-J interval is outside of the BB-J interval standard value range, displaying the length of the BB-J interval in a different color and sounding an audible alarm using the display device.

15. The method of claim 13, further comprising
identifying a BB to ST segment (B-ST) interval from the comparison using the processor,
calculating a length of the BB-ST interval in time using the processor, and
displaying the ECG waveform with the BB-ST interval annotated and displays the length of the BB-ST interval in time for the at least one heartbeat of the beating heart using the display device.

16. The method of claim 13, further comprising
identifying an i-R segment between an initial end of the Purkinje's fibers (I-point) to a maximum peak of ventricular depolarization (R) from the comparison using the processor,
calculating a length of the i-R segment in time using the processor, and displaying the ECG waveform with the i-R segment annotated and displays the length of the i-R segment in time for the at least one heartbeat of the beating heart using the display device.

17. The method of claim 13, further comprising identifying an R-j segment between a maximum peak of ventricular depolarization (R) and a terminal end of the Purkinje's fibers (J-Point) from the comparison using the processor, calculating a length of the R-j segment in time using the processor, and displaying the ECG waveform with the R-j segment annotated and displays the length of the R-j segment in time for the at least one heartbeat of the beating heart using the display device.

18. The method of claim 13, further comprising identifying a J-Tp segment between a terminal end of the Purkinje's fibers (J-point) and a maximum peak of ventricular repolarization (Tp) from the comparison using the processor, calculating a length of the J-Tp segment in time using the processor, and displaying the ECG waveform with the J-Tp segment annotated and displays the length of the J-Tp segment in time for the at least one heartbeat of the beating heart using the display device.

19. The method of claim 13, further comprising identifying a T-T interval between a maximum peak of ventricular repolarization (Tp) of a first heartbeat and a maximum peak of ventricular repolarization (Tp) of a second heartbeat from the comparison using the processor, calculating a length of the T-T interval in time using the processor, and displaying the ECG waveform with the T-T interval annotated and displays the length of the T-T interval in time for the at least one heartbeat of the beating heart using the display device.

20. An invasive electrocardiography (ECG) system for displaying and measuring intervals and segments of an ECG waveform during measurement of the ECG waveform, comprising:

two or more electrodes placed directly on the surface of a beating heart of a patient that receive electrical impulses from the beating heart;

a detector that detects the electrical impulses from at least one pair of electrodes of the two or more electrodes and converts the electrical impulses to an ECG waveform for each heartbeat of the beating heart;

a processor that receives the ECG waveform for at least one heartbeat from the detector, converts the ECG waveform to a frequency domain waveform, separates the frequency domain waveform into two or more different frequency domain waveforms, and converts the two or more different frequency domain waveforms into a plurality of time domain cardiac electrophysiological subwaveforms and discontinuity points between these subwaveforms of the ECG waveform, compares the plurality of subwaveforms and discontinuity points to a database of subwaveforms and discontinuity points for cardiac electrophysiological signals of ECG waveforms for a plurality of known and normal and abnormal patients or to a set of rules developed from the database, calculates a length of the BB-J interval in time, and identifies a bundle branches (BB) to J-Point (BB-J) interval from the comparison; and a display device that displays the ECG waveform with the BB-J interval annotated and displays the length of the BB-J interval in time for the at least one heartbeat of the beating heart.

* * * * *